(12) United States Patent
Hufton et al.

(10) Patent No.: US 9,523,092 B2
(45) Date of Patent: Dec. 20, 2016

(54) COMPATIBLE DISPLAY VECTOR SYSTEMS

(71) Applicant: Wyeth LLC, Madison, NJ (US)

(72) Inventors: Simon Evan Hufton, Hitchin (GB); William James Jonathan Finlay, Dublin (IR)

(73) Assignee: Wyeth LLC, New York, NY (US)

( * ) Notice: Subject to any disclaimer, the term of this patent is extended or adjusted under 35 U.S.C. 154(b) by 739 days.

(21) Appl. No.: 13/651,621

(22) Filed: Oct. 15, 2012

(65) Prior Publication Data
US 2013/0217597 A1   Aug. 22, 2013

Related U.S. Application Data

(63) Continuation of application No. 12/566,854, filed on Sep. 25, 2009, now Pat. No. 8,313,942.

(60) Provisional application No. 61/100,432, filed on Sep. 26, 2008.

(51) Int. Cl.
| | | |
|---|---|---|
| *C12N 15/63* | (2006.01) | |
| *C12N 15/85* | (2006.01) | |
| *C12N 15/10* | (2006.01) | |

(52) U.S. Cl.
CPC ....... *C12N 15/1041* (2013.01); *C12N 15/1037* (2013.01)

(58) Field of Classification Search
None
See application file for complete search history.

(56) References Cited

U.S. PATENT DOCUMENTS

| | | | |
|---|---|---|---|
| 5,223,409 | A | 6/1993 | Ladner et al. |
| 5,643,768 | A | 7/1997 | Kawasaki et al. |
| 5,658,754 | A | 8/1997 | Kawasaki et al. |
| 7,074,557 | B2 | 7/2006 | Osborn et al. |
| 2003/0118592 | A1 | 6/2003 | Ledbetter et al. |
| 2003/0133939 | A1 | 7/2003 | Ledbetter et al. |
| 2003/0224408 | A1 | 12/2003 | Hoogenboom et al. |
| 2004/0058445 | A1 | 3/2004 | Ledbetter et al. |
| 2005/0136049 | A1 | 6/2005 | Ledbetter et al. |
| 2005/0175614 | A1 | 8/2005 | Ledbetter et al. |
| 2005/0180970 | A1 | 8/2005 | Ledbetter et al. |
| 2005/0186216 | A1 | 8/2005 | Ledbetter et al. |
| 2005/0202012 | A1 | 9/2005 | Ledbetter et al. |
| 2005/0202023 | A1 | 9/2005 | Ledbetter et al. |
| 2005/0202028 | A1 | 9/2005 | Ledbetter et al. |
| 2005/0202534 | A1 | 9/2005 | Ledbetter et al. |
| 2005/0238646 | A1 | 10/2005 | Ledbetter et al. |
| 2007/0286585 | A1 | 12/2007 | Moon et al. |
| 2007/0286858 | A1 | 12/2007 | Clancy et al. |
| 2008/0107601 | A1 | 5/2008 | Lauwereys et al. |

FOREIGN PATENT DOCUMENTS

| | | |
|---|---|---|
| WO | WO90/02809 | 3/1990 |
| WO | WO92/09690 | 6/1991 |
| WO | WO91/17271 | 11/1991 |
| WO | WO92/01047 | 1/1992 |
| WO | WO92/15679 | 9/1992 |
| WO | WO92/18619 | 10/1992 |
| WO | WO92/20791 | 11/1992 |
| WO | WO93/01288 | 1/1993 |
| WO | WO2007/109749 | 9/2007 |

OTHER PUBLICATIONS

Rakonjac and Conway (Microbial Bionanotechnology: Biological Self-assembly Systems and Biopolymer-based Nanostructures, copy right 2006. Edited by Bernd Rehm, Chapter 7 Bacteriophages: assembly and Application).*
Falcone and Andrews (Molecular and Cellular Biology, 1991. vol. 11, No. 5, pp. 2656-2664).*
Zelenetz et al, "Directional cloning of cDNA using a selectable Sfil cassette" Gene, vol. 89, No. 1 pp. 123-127, Apr. 1990, Elsevier, Amsterdam, NL.
Hanes and A. Pluckthun, "In vitro selection and evolution of functional proteins by using ribosome display" Proceedings of the National Academy of Science, vol. 94, pp. 4937-4942, May 1997.
He et al. "Antibody-ribosome-mRNA (ARM) complexes as efficient selection particles for in vitro display and ecolution of antibody combing sites" Nucleic Acids Research, Oxford University Press, Surrey, GB, No. 24 pp. 5132-5134, Dec. 1997.
Hogenboom et al. "Antibody phage display technology and its applications" Immunotechnology, Elsevier Science Publishers BV, NL, vol. 4 No. 1 pp. 1-20 Jun. 1998.
Groves et al. "Affinity maturation of phage display antibody populations using ribosome display" J. of Immunological Methods, Elsevier Science Publishers BV, Amsterdam, NL vol. 313 No. 1-2, pp. 129-139, Jun. 2006.
Groves et al. "Applications of ribosome display to antibody drug discovery" Expert Opinion on Biological: Therapy, Informa Healthcare, UK, vol. 5, No. 1, pp. 125-135, Jan. 2005.
Wada Akira et al., "Ribosome Display Selection of a Metal-Binding Motif From an Artificial Peptide Library", Biotechnology and Bioengineering, vol. 101, No. 5, pp. 1102-1107, Dec. 2008.
Finlay et al. "Affinity Maturation of a Humanized Rat Antibody for Anti-RAGE Therapy: Comprehensive Mutagenesis Reveals a High Level of Mutational Plasticity Both Inside and Outside the Complementarity-Determining Regions" Journal of Molecular Biology, vol. 388, No. 3, pp. 541-558, London, GB, May 2009.
PCT International Search Report and Written Opinion, PCT/US2009/058316, Jun. 8, 1010.
Santini et al., J. Mol. Bio 282: 125-135 (1998).
Houshmand et al., Annals Biochem 268: 363-370 (1999).

(Continued)

*Primary Examiner* — Celine Qian
(74) *Attorney, Agent, or Firm* — John Miller; Raquel M. Alvarez

(57) ABSTRACT

The present invention provides a polynucleotide vector system used during polypeptide display that can be used to facilitate transfer of pools of polynucleotides encoding antigen binding proteins of interest. The present invention also provides methods that allow seamless conversion of pools of polynucleotides encoding antigen binding proteins using a restriction enzyme digestion and ligation strategy.

10 Claims, 10 Drawing Sheets

(56) References Cited

OTHER PUBLICATIONS

Smith et al., Science 228:1315-1317 (1985).
de Haard et al., J. Biol. Chem 274: 18218-30 (1999).
Hoogenboom et al., Immunotechnology 4: 1-20 (1998).
Hoogenboom et al., Immunol. Today 21:371-8 (2000).
Fuchs et al., Bio/Technology 9: 1370-1372 (1991).
Hay et al., Hum. Antibod Hybridomas 3: 81-85 (1992).
Huse et al., Science 246: 1275-1281 (1989).
Griffiths et al., EMBO J 12: 725-734 (1993).
Hawkins et al., J Mol Biol., 226: 889-96 (1992).
Clackson et al., Nature 352: 624-628 (1991).
Gram et al., PNAS 89 :3576-3580 (1992).
Garrard et al., BioTechnology 9:1373-1377 (1991).
Rebar et al., Methods Enzymol. 267: 129-149 (1996).
Hoogenboom et al., Nucleic Acid Research 19: 4133-4137 (1991).
Barbas et al., PNAS 88:7978-7982 (1991).
Gersuk et al., Biochem. and Biophys. Res. Com. 232:578-582 (1997).
Hanes and Pluckthun, PNAS 94: 4937-4942 (1997).
Hanes, PNAS 95: 14130-14150 (1998).
He and Taussig, Nucleic Acid Research 25: 5132-5134 (1997).
VauQhn et al. Nature BiotechnoloQY 16, 535-539 (1998).
Sheets MD et al., Proc Natl Acad Sci USA 95: 6157-6162 (1998).
Pini, A., J. Biol. Chem. 273 p. 21769 (1998).
Knappik, A., J. Mol. Biol. 296: 57-86 (2000).
Sblattero and. Bradbury, Nat. Biotechnol. 18 (2000), p. 75.
Kolonin et al., Current Opinion in Chemical Biology 5: 308-313 (2001).
Pasqualini and Ruoslahti, Nature 380:364-366 (1996).
Pasqualini et al., "In vivo Selection of Phage Display Libraries" in Phage Display: A Laboratory Manual, Cold Spring Harbor Press 22.1-22.24 (2000).
Harlow and Lane, Antibodies: A Laboratory Manual, Cold Spring Harbor Laboratory, New York (1988).
Stemmer W.P. Nature 370: 389-391 (1994).
Coco et al., Nature Biotech 19 p. 354 (2001).
Zoller et al., Methods Enzymol. 154:329-50 (1987).
Reidhaar-Olson, Methods Enzymol. 208:564-586 (1991).
Pluckthun, BioTechnology 9:545-551 (1991).
Ref, Current Opinion Biotech 4: 573-576 (1993).
Trill J et al., Current Opinion Biotech 6: 553-560 (1995).

* cited by examiner

SEQUENCE LISTING

<160> NUMBER OF SEQ ID NOS: 51

<210> SEQ ID NO 1
<211> LENGTH: 4513
<212> TYPE: DNA
<213> ORGANISM: Artificial
<220> FEATURE:
<223> OTHER INFORMATION: Synthetic Plasmid pWRIL-1

<400> SEQUENCE: 1

```
ccgatcgccc ttcccaacag ttgcgcagcc tgaatggcga atgggacgcg ccctgtagcg      60
gcgcattaag cgcggcgggt gtggtggtta cgcgcagcgt gaccgctaca cttgccagcg     120
ccctagcgcc cgctcctttc gctttcttcc cttcctttct cgccacgttc gccggctttc     180
cccgtcaagc tctaaatcgg gggctccctt tagggttccg atttagagct ttacggcacc     240
tcgaccgcaa aaacttgat ttgggtgatg gttcacgtag tgggccatcg ccctgataga     300 cggttttcg ccctttgacg ttggagtcca cgttctttaa tagtggactc ttgttccaaa     360
ctggaacaac actcaaccct atcgcggtct attcttttga tttataaggg attttgccga     420
tttcggccta ttggttaaaa aatgagctga tttaacaaat atttaacgcg aattttaaca     480
aaatattaac gtttacaatt tcgcctgatg cggtattttc tccttacgca tctgtgcggt     540
atttcacacc gcatacaggt ggcactttc ggggaaatgt gcgcggaacc cctatttgtt     600
tattttctta aatacattca aatatgtatc cgctcatgag acaataaccc tgataaatgc     660
ttcaataata ttgaaaaagg aagagtatga gtattcaaca tttccgtgtc gcccttattc     720
ccttttttgc ggcattttgc cttcctgttt ttgctcaccc agaaacgctg gtgaaagtaa     780
aagatgctga agatcagttg ggtgctcggg tgggttacat cgaactggat ctcaacagcg     840
```

```
gtaagatcct tgagagtttt cgccccgaag aacgttttcc aatgatgagc acttttaaag    900
ttctgctatg tggcgcggta ttatcccgta ttgacgccgg gcaagagcaa ctcggtcgcc    960
gcatacacta ttctcagaat gacttggttg agtactcacc agtcacagaa aagcatctta   1020
cggatggcat gacagtaaga gaattatgca gtgctgccat aaccatgagt gataacactg   1080
cggccaactt acttctgaca acgatcggag gaccgaagga gctaaccgct ttttgcaca    1140 acatggggga tcatgtaact cgccttgatc gttgggaacc ggagctgaat gaagccatac   1200
caaacgacga gagtgacacc acgatgcctg tagcaatgcc aacaacgttg cgcaaactat   1260
taactggcga actacttact ctagcttccc ggcaacaatt aatagactgg atggaggcgg   1320
ataaagttgc aggaccactt ctgcgctcgg cccttccggc tggctggttt attgctgata   1380
aatctggagc cggtgagcgt gggtctcgcg gtatcattgc agcactgggg ccagatggta   1440
agcgctcccg tatcgtagtt atctacacga cggggagtca ggcaactatg gatgaacgaa   1500
atagacagat cgctgagata ggtgcctcac tgattaagca ttggtaactg tcagaccaag   1560
tttactcata tatactttag attgatttaa aacttcattt ttaatttaaa aggatctagg   1620
tgaagatcct ttttgataat ctcatgacca aaatccctta acgtgagttt cgttccact    1680 gagcgtcaga ccccgtagaa aagatcaaag gatcttcttg agatcctttt tttctgcgcg   1740
taatctgctg cttgcaaaca aaaaaaccac cgctaccagc ggtggtttgt ttgccggatc   1800
aagagctacc aactcttttt ccgaaggtaa ctggcttcag cagagcgcag ataccaaata   1860
ctgtccttct agtgtagccg tagttaggcc accacttcaa gaactctgta gcaccgccta   1920
catacctcgc tctgctaatc ctgttaccag tggctgctgc cagtggcgat aagtcgtgtc   1980
ttaccgggtt ggactcaaga cgatagttac cggataaggc gcagcggtcg gctgaacgg    2040 ggggttcgag cacacagccc agcttggagc gaacgaccta caccgaactg agatacctac   2100
agcgtgagct atgagaaagc gccacgcttc ccgaagggag aaaggcggac aggtatccgg   2160
taagcggcag ggtcggaaca ggagagcgca cgagggagct tccaggggga aacgcctggt   2220
atctttatag tcctgtcggg tttcgccacc tctgacttga gcgtcgattt ttgtgatgct   2280
cgtcaggggg gcggagccta tggaaaaacg ccagcaacgc ggccttttta cggttcctgg   2340
gcttttgctg gccttttgct cacatgttct ttcctgcgtt atccctgat tctgtggata    2400 accgtattac cgcctttgag tgagctgata ccgctcgccg cagccgaacg accgagcgca   2460
gcgagtcagt gagcgaggaa gcggaagagc gcccaatacg caaaccgcct ctccccgcgc   2520
gttggccgat tcattaatgc agctggcacg acaggtttcc cgactggaaa gcgggcagtg   2580
agcgcaacgc aattaatgtg agttagctca ctcattaggc accccaggct ttacacttta   2640
tgcttccggc tcgtatgttg tgtggaattg tgagcggata caattgaat tcaggaggaa    2700 tttaaaatga aaagacagc tatcgcgatt gcagtggcac tggctggttt cgctaccgtg    2760
gcccaggcgg ccccccctatt tgtttatttt tctaaataca ttcaaatatg tatccgctca   2820
tgagacaata accctgataa atgcttcaat aatgtgagga gggccaccat ggagaaaaaa   2880
atcactggat ataccaccgt tgatatatcc caatggcatc gtaaagaaca ttttgaggca   2940
tttcagtcag ttgctcaatg tacctataac cagaccgttc agctggatat tacggccttt   3000
ttaaagaccg taaagaaaaa taagcacaag ttttatccgg cctttattca cattcttgcc   3060
cgcctgatga atgctcatcc ggagttccgt atggcaatga agacggtga gctggtgata    3120 tgggatagtg ttcacccttg ttacaccgtt ttccatgagc aaactgaaac gttttcatcg   3180
ctctggagtg aataccacga cgatttccgg cagtttctac acatatattc gcaagatgtg   3240
```

```
gcgtgttacg gtgaaaacct ggcctatttc cctaaagggt ttattgagaa tatgttttc     3300 gtctcagcca atccctgggt gagtttcacc agttttgatt taaacgtggc caatatggac    3360
aacttcttcg cccccgtttt caccatgggc aaatattata cgcaaggcga caaggtgctg    3420
atgccgctgg cgattcaggt tcatcatgcc gtctgtgatg gcttccatgt cggcagaatg    3480
cttaatgaat tacaacagta ctgcgatgag tggcagggcg gggcgtaaat ggccaagtga    3540
tgattgacca gtgccgttcc ggtgctcacc gcgtgagacg tcgccggagc ggtcgagttc    3600
tggaccgacc ggctcgggtt ctcccgggac ttcgtggagg acgacttcgc cggtgtggtc    3660
cgggacgacg tgaccctgtt catcagcgcg gtccaggacc aggtggtgcc ggacaacacc    3720
ctggcctggg tgtgggtgcg cggcctggac gagctgtacg ccgagtggtc ggaggtcgtg    3780
tccacgaact tccgggacgc ctccgggccg gccatgaccg agatcggcga gcagccgtgg    3840
gggcgggagt tcgccctgcg cgacccggcc ggcaactgcg tgcacttcgt ggccgaggag    3900
caggactgag gcctcagggg cccaccatca ccatcaccat ggcgcagaat tcgagcagaa    3960
gctgatctct gaggaagacc tgtagggtgg tggctctggt tccggtgatt tgattatga    4020 aaagatggca aacgctaata aggggggctat gaccgaaaat gccgatgaaa acgcgctaca    4080
gtctgacgct aaaggcaaac ttgattctgt cgctactgat tacggtgctg ctatcgatgg    4140
tttcattggt gacgtttccg gccttgctaa tggtaatggt gctactggtg attttgctgg    4200
ctctaattcc caaatggctc aagtcggtga cggtgataat tcacctttaa tgaataattt    4260
ccgtcaatat ttaccttccc tccctcaatc ggttgaatgt cgcccttttg tctttagcgc    4320
tggtaaacca tatgaatttt ctattgattg tgacaaaata aacttattcc gtggtgtctt    4380
tgcgtttctt ttatatgttg ccacctttat gtatgtattt tctacgtttg ctaacatact    4440
gcgtaataag gagtcttaag ctagctaatt aatttaagcg gccgcagatc tgggaaattg    4500
taagcgttaa tat                                                       4513

<210> SEQ ID NO 2
<211> LENGTH: 4605
<212> TYPE: DNA
<213> ORGANISM: Artificial
<220> FEATURE:
<223> OTHER INFORMATION: Synthetic Plasmid pWRIL-2

<400> SEQUENCE: 2
ccgatcgccc ttcccaacag ttgcgcagcc tgaatggcga atgggacgcg ccctgtagcg      60
gcgcattaag cgcggcgggt gtggtggtta cgcgcagcgt gaccgctaca cttgccagcg     120
ccctagcgcc cgctcctttc gctttcttcc cttcctttct cgccacgttc gccggctttc     180
cccgtcaagc tctaaatcgg gggctccctt tagggttccg atttagagct ttacggcacc     240
tcgaccgcaa aaaacttgat ttgggtgatg gttcacgtag tgggccatcg ccctgataga     300
cggtttttcg ccctttgacg ttggagtcca cgttctttaa tagtggactc ttgttccaaa     360
ctggaacaac actcaaccct atcgcggtct attcttttga tttataaggg attttgccga    420
tttcggccta ttggttaaaa aatgagctga tttaacaaat atttaacgcg aattttaaca    480
aaatattaac gtttacaatt tcgcctgatg cggtattttc tccttacgca tctgtgcggt    540
atttcacacc gcatacaggt ggcactttc ggggaaatgt gcgcggaacc cctatttgtt    600
tatttttcta aatacattca aatatgtatc cgctcatgag acaataaccc tgataaatgc    660
ttcaataata ttgaaaaagg aagagtatga gtattcaaca tttccgtgtc gcccttattc    720
```

```
ccttttttgc ggcattttgc cttcctgttt ttgctcaccc agaaacgctg gtgaaagtaa    780
aagatgctga agatcagttg ggtgcacgag tgggttacat cgaactggat ctcaacagcg    840
gtaagatcct tgagagtttt cgccccgaag aacgttttcc aatgatgagc acttttaaag    900
ttctgctatg tggcgcggta ttatcccgta ttgacgccgg gcaagagcaa ctcggtcgcc    960
gcatacacta ttctcagaat gacttggttg agtactcacc agtcacagaa aagcatctta   1020
cggatggcat gacagtaaga gaattatgca gtgctgccat aaccatgagt gataacactg   1080
cggccaactt acttctgaca acgatcggag gaccgaagga gctaaccgct tttttgcaca   1140
acatggggga tcatgtaact cgccttgatc gttgggaacc ggagctgaat gaagccatac   1200
caaacgacga gagtgacacc acgatgcctg tagcaatgcc aacaacgttg cgcaaactat   1260
taactggcga actacttact ctagcttccc ggcaacaatt aatagactgg atggaggcgg   1320
ataaagttgc aggaccactt ctgcgctcgg cccttccggc tggctggttt attgctgata   1380
aatctggagc cggtgagcgt gggtctcgcg gtatcattgc agcactgggg ccagatggta   1440
agcgctcccg tatcgtagtt atctacacga cggggagtca ggcaactatg gatgaacgaa   1500
atagacagat cgctgagata ggtgcctcac tgattaagca ttggtaactg tcagaccaag   1560
tttactcata tactttag attgatttaa aacttcattt ttaatttaaa aggatctagg   1620
tgaagatcct ttttgataat ctcatgacca aaatccctta acgtgagttt tcgttccact   1680
gagcgtcaga ccccgtagaa aagatcaaag gatcttcttg agatcctttt tttctgcgcg   1740
taatctgctg cttgcaaaca aaaaaaccac cgctaccagc ggtggtttgt ttgccggatc   1800
aagagctacc aactcttttt ccgaaggtaa ctggcttcag cagagcgcag ataccaaata   1860
ctgtccttct agtgtagccg tagttaggcc accacttcaa gaactctgta gcaccgccta   1920
catacctcgc tctgctaatc ctgttaccag tggctgctgc cagtggcgat aagtcgtgtc   1980
ttaccgggtt ggactcaaga cgatagttac cggataaggc gcagcggtcg ggctgaacgg   2040
ggggttcgtg cacacagccc agcttggagc gaacgaccta caccgaactg agatacctac   2100
agcgtgagct atgagaaagc gccacgcttc ccgaagggag aaaggcggac aggtatccgg   2160
taagcggcag ggtcggaaca ggagagcgca cgagggagct tccaggggga aacgcctggt   2220
atctttatag tcctgtcggg tttcgccacc tctgacttga gcgtcgattt ttgtgatgct   2280
cgtcaggggg gcggagccta tggaaaaacg ccagcaacgc ggccttttta cggttcctgg   2340
cttttgctgg ccttttgctc acatgttct ttcctgcgtt atccctgat tctgtggata   2400 accgtattac cgcctttgag tgagctgata ccgctcgccg cagccgaacg accgagcgca   2460
gcgagtcagt gagcgaggaa gcggaagagc gcccaatacg caaaccgcct ctccccgcgc   2520
gttggccgat tcattaatgc agctggcacg acaggtttcc cgactggaaa gcgggcagtg   2580
agcggtaccc gataaaagcg gcttcctgac aggaggccgt tttgttttgc agcccacctc   2640
aacgcaatta atgtgagtta gctcactcat taggcacccc aggctttaca ctttatgctt   2700
ccggctcgta tgttgtgtgg aattgtgagc ggataacaat ttcacacagg aaacagctat   2760
gaccatgatt acgaatttct agataacgag ggcaaatcat gaaaaagaca gctatcgcga   2820
ttgcagtggc actggctggt ttcgctaccg tgcccaggc ggccccccta tttgtttatt   2880
tttctaaata cattcaaata tgtatccgct catgagacaa taaccctgat aaatgcttca   2940
ataatgtgag gagggccacc atggagaaaa aaatcactgg atataccacc gttgatatat   3000
cccaatggca tcgtaaagaa catttttgagg catttcagtc agttgctcaa tgtacctata   3060
accagaccgt tcagctggat attacggcct ttttaaagac cgtaaagaaa aataagcaca   3120
```

```
agttttatcc ggcctttatt cacattcttg cccgcctgat gaatgctcat ccggagttcc    3180
gtatggcaat gaaagacggt gagctggtga tatgggatag tgttcaccct tgttacaccg    3240
ttttccatga gcaaactgaa acgttttcat cgctctggag tgaataccac gacgatttcc    3300
ggcagtttct acacatatat tcgcaagatg tggcgtgtta cggtgaaaac ctggcctatt    3360
tccctaaagg gtttattgag aatatgtttt tcgtctcagc caatccctgg gtgagtttca    3420
ccagttttga tttaaacgtg gccaatatgg acaacttctt cgcccccgtt ttcaccatgg    3480
gcaaatatta tacgcaaggc gacaaggtgc tgatgccgct ggcgattcag gttcatcatg    3540
ccgtctgtga tggcttccat gtcggcagaa tgcttaatga attacaacag tactgcgatg    3600
agtggcaggg cggggcgtaa atggccaagt gatgattgac cagtgccgtt ccggtgctca    3660
ccgcgtgaga cgtcgccgga gcggtcgagt tctggaccga ccggctcggg ttctcccggg    3720
acttcgtgga ggacgacttc gccggtgtgg tccgggacga cgtgaccctg ttcatcagcg    3780
cggtccagga ccaggtggtg ccggacaaca ccctggcctg ggtgtgggtg cgcggcctgg    3840
acgagctgta cgccgagtgg tcggaggtcg tgtccacgaa cttccgggac gcctccgggc    3900
cggccatgac cgagatcggc gagcagccgt ggggcggga gttcgccctg cgcgacccgg    3960
ccggcaactg cgtgcacttc gtggccgagg agcaggactg aggcctcagg ggcccaccat    4020
caccatcacc atggcgcaga attcgagcag aagctgatct ctgaggaaga cctgtagggt    4080
ggtggctctg gttccggtga ttttgattat gaaaagatgg caaacgctaa taaggggggct    4140 atgaccgaaa atgccgatga aaacgcgcta cagtctgacg ctaaaggcaa acttgattct    4200
gtcgctactg attacggtgc tgctatcgat ggttcattg gtgacgttc cggccttgct    4260 aatggtaatg tgctactgg tgattttgct ggctctaatt cccaaatggc tcaagtcggt    4320
gacggtgata attcaccttt aatgaataat ttccgtcaat atttaccttc cctccctcaa    4380
tcggttgaat gtcgcccttt tgtctttagc gctggtaaac catatgaatt ttctattgat    4440
tgtgacaaaa taaacttatt ccgtggtgtc tttgcgtttc ttttatatgt tgccacctt    4500 atgtatgtat tttctacgtt tgctaacata ctgcgtaata aggagtctta agctagctaa    4560
ttaatttaag cggccgcaga tctgggaaat tgtaagcgtt aatat                   4605
```

<210> SEQ ID NO 3
<211> LENGTH: 3034
<212> TYPE: DNA
<213> ORGANISM: Artificial
<220> FEATURE:
<223> OTHER INFORMATION: Synthetic Plasmid pWRIL-3

<400> SEQUENCE: 3

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcgggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt catacgaaat taatacgact     420
cactataggg agaccacaac ggtttccctc tagaaataat tttgtttaac tttaagaagg     480
agatatatcc atggactaca agacgtggcc ccaggcggcc ggcgcgcact ccgatgtcct     540
```

```
ctgatcaggc ctcagggcc gagggcggcg ttctggttc cggtgatttt gattatgaaa      600
agatggcaaa cgctaataag ggggctatga ccgaaaatgc cgatgaaaac gcgctacagt    660
ctgacgctaa aggcaaactt gattctgtcg ctactgatta cggtgctgct atcgatggtt    720
tcattggtga cgtttccggc cttgctaatg gtaatggtgc tactggtgat accgcacacc    780
ttactggtgt gcggaagctt ggcgtaatca tggtcatagc tgtttcctgt gtgaaattgt    840
tatccgctca caattccaca acatacga gccggaagca taagtgtaa agcctggggt       900
gcctaatgag tgagctaact cacattaatt gcgttgcgct cactgcccgc tttccagtcg    960
ggaaacctgt cgtgccagct gcattaatga atcggccaac gcgcggggag aggcggtttg   1020
cgtattgggc gctcttccgc ttcctcgctc actgactcgc tgcgctcggt cgttcggctg   1080
cggcgagcgg tatcagctca ctcaaaggcg gtaatacggt tatccacaga atcaggggat   1140
aacgcaggaa agaacatgtg agcaaaaggc cagcaaaagg ccaggaaccg taaaaaggcc   1200
gcgttgctgg cgtttttcca taggctccgc cccctgacg agcatcacaa aaatcgacgc    1260
tcaagtcaga ggtggcgaaa cccgacagga ctataaagat accaggcgtt tccccctgga   1320
agctccctcg tgcgctctcc tgttccgacc ctgccgctta ccggatacct gtccgccttt   1380
ctcccttcgg gaagcgtggc gctttctcat agctcacgct gtaggtatct cagttcggtg   1440
taggtcgttc gctccaagct gggctgtgtg cacgaacccc ccgttcagcc cgaccgctgc   1500
gccttatccg gtaactatcg tcttgagtcc aacccggtaa gacacgactt atcgccactg   1560
gcagcagcca ctggtaacag gattagcaga gcgaggtatg taggcggtgc tacagagttc   1620
ttgaagtggt ggcctaacta cggctacact agaaggacag tatttggtat ctgcgctctg   1680
ctgaagccag ttaccttcgg aaaaagagtt ggtagctctt gatccggcaa caaaccacc    1740
gctggtagcg gtggtttttt tgtttgcaag cagcagatta cgcgcagaaa aaaggatct    1800
caagaagatc ctttgatctt ttctacgggg tctgacgctc agtggaacga aaactcacgt   1860
taagggattt tggtcatgag attatcaaaa aggatcttca cctagatcct tttaaattaa   1920
aaatgaagtt ttaaatcaat ctaaagtata tatgagtaaa cttggtctga cagttaccaa   1980
tgcttaatca gtgaggcacc tatctcagcg atctgtctat ttcgttcatc catagttgcc   2040
tgactccccg tcgtgtagat aactacgata cgggagggct taccatctgg ccccagtgct   2100
gcaatgatac cgcgagaccc acgctcaccg gctccagatt tatcagcaat aaaccagcca   2160
gccggaaggg ccgagcgcag aagtggtcct gcaactttat ccgcctccat ccagtctatt   2220
aattgttgcc gggaagctag agtaagtagt tcgccagtta atagtttgcg caacgttgtt   2280
gccattgcta caggcatcgt ggtgtcacgc tcgtcgtttg gtatggcttc attcagctcc   2340
ggttcccaac gatcaaggcg agttacatga tcccccatgt tgtgcaaaaa agcggttagc   2400
tccttcggtc ctccgatcgt tgtcagaagt aagttggccg cagtgttatc actcatggtt   2460
atggcagcac tgcataattc tcttactgtc atgccatccg taagatgctt ttctgtgact   2520
ggtgagtact caaccaagtc attctgagaa tagtgtatgc ggcgaccgag ttgctcttgc   2580
ccggcgtcaa tacgggataa taccgcgcca catagcagaa ctttaaaagt gctcatcatt   2640
ggaaaacgtt cttcggggcg aaaactctca aggatcttac cgctgttgag atccagttcg   2700
atgtaaccca ctcgtgcacc caactgatct tcagcatctt ttactttcac cagcgtttct   2760
gggtgagcaa aaacaggaag gcaaaatgcc gcaaaaaagg gaataagggc gacacggaaa   2820
tgttgaatac tcatactctt cctttttcaa tattattgaa gcatttatca gggttattgt   2880
ctcatgagcg gatacatatt tgaatgtatt tagaaaaata aacaaatagg ggttccgcgc   2940
```
acatttcccc gaaaagtgcc acctgacgtc taagaaacca ttattatcat gacattaacc     3000
tataaaaata ggcgtatcac gaggcccttt cgtc                                 3034

<210> SEQ ID NO 4
<211> LENGTH: 3755
<212> TYPE: DNA
<213> ORGANISM: Artificial
<220> FEATURE:
<223> OTHER INFORMATION: Synthetic plasmid pWRIL-4

<400> SEQUENCE: 4
tcgcgcgttt cggtgatgac ggtgaaaacc tctgacacat gcagctcccg gagacggtca       60
cagcttgtct gtaagcggat gccgggagca gacaagcccg tcagggcgcg tcagcgggtg      120
ttggcgggtg tcggggctgg cttaactatg cggcatcaga gcagattgta ctgagagtgc      180
accatatgcg gtgtgaaata ccgcacagat gcgtaaggag aaaataccgc atcaggcgcc      240
attcgccatt caggctgcgc aactgttggg aagggcgatc ggtgcgggcc tcttcgctat      300
tacgccagct ggcgaaaggg ggatgtgctg caaggcgatt aagttgggta acgccagggt      360
tttcccagtc acgacgttgt aaaacgacgg ccagtgaatt catacgaaat taatacgact      420
cactatagaa tacaagcttc ttgttctttt tgcagaagct cagaataaac gctcaacttt      480
ggcagatcta ccatggacta caaagacgtg gcccaggcgg ccggcgcgca ctccgaaatt      540
gtgttgacac agtctccagc caccctgtct ttgtctccag gtgaaagagc caccctctcc      600
tgcagggcca gttccagtgt tagctacatt gtttggtacc aacagaaacc tggccaggca      660
cctaggctcc tcatctatgc cccatccaac ctggcttctg ggattccagc caggttcagt      720
ggcagtggat ccgggacaga cttcactctc accatcagca gtctagagcc tgaagatttt      780
gcagtttatt actgtcagca gtggagtttt aaccctccca cgttcggcca agggaccaag      840
gtggaaatca aagatggcgg tggatcgggc ggtggtggat ctggaggagg tgggagctct      900
caggtgcagc tggtgcagtc tggtgctgag agcaagaagc tggggcctc agtgaaggtt       960 tcctgcaagg ctagcggata caccttcacc agctacaata tgcactgggt gcgacaggcg     1020
cctggacaag gctcgagtg gatgggagct atctatcctg gaaatggtga tacatcctac     1080
aatcagaagt tcaagggcag ggtcaccatg accagagaca cgtccacgag cacagtctac     1140
atggagctga gcagcctgag atctgaggac acggccgtgt attactgtgc ccgaagctac     1200
tatagtaact cttactggta cttcgatctc tggggccgcg gcaccctggt cactgtctcc     1260
tctgatcagg cctcagggc cgagggcggc ggttctggtt ccggtgattt tgattatgaa     1320 agatggcaa cgctaataa gggggctatg accgaaaatg ccgatgaaaa cgcgctacag     1380
tctgacgcta aaggcaaact tgattctgtc gctactgatt acggtgctgc tatcgatggt     1440
ttcattggtg acgtttccgg ccttgctaat ggtaatggtg ctactggtga taccgcacac     1500
cttactggta tgcggaagct tggcgtaatc atggtcatag ctgtttcctg tgtgaaattg     1560
ttatccgctc acaattccac acaacatacg agccggaagc ataaagtgta agcctggggt      1620
tgcctaatga gtgagctaac tcacattaat tgcgttgcgc tcactgcccg ctttccagtc     1680
gggaaacctg tcgtgccagc tgcattaatg aatcggccaa cgcgcgggga gaggcggttt     1740
gcgtattggg cgctcttccg cttcctcgct cactgactcg ctgcgctcgg tcgttcggct     1800
gcggcgagcg gtatcagctc actcaaaggc ggtaatacgg ttatccacag aatcaggga     1860 taacgcagga aagaacatgt gagcaaaagg ccagcaaaag gccaggaacc gtaaaaaggc     1920

```
cgcgttgctg gcgttttcc  ataggctccg ccccctgac  gagcatcaca aaaatcgacg   1980
ctcaagtcag aggtggcgaa acccgacagg actataaaga taccaggcgt ttccccctgg   2040
aagctccctc gtgcgctctc ctgttccgac cctgccgctt accggatacc tgtccgcctt   2100
tctcccttcg ggaagcgtgg cgctttctca tagctcacgc tgtaggtatc tcagttcggt   2160
gtaggtcgtt cgctccaagc tgggctgtgt gcacgaaccc cccgttcagc ccgaccgctg   2220
cgccttatcc ggtaactatc gtcttgagtc aacccggta  agacacgact tatcgccact   2280
ggcagcagcc actggtaaca ggattagcag agcgaggtat gtaggcggtg ctacagagtt   2340
cttgaagtgg tggcctaact acggctacac tagaaggaca gtatttggta tctgcgctct   2400
gctgaagcca gttaccttcg gaaaaagagt tggtagctct tgatccggca aacaaaccac   2460
cgctggtagc ggtggttttt tgtttgcaa  gcagcagatt acgcgcagaa aaaaggatc   2520 tcaagaagat cctttgatct tttctacggg gtctgacgct cagtggaacg aaaactcacg   2580
ttaagggatt ttggtcatga gattatcaaa aaggatcttc acctagatcc ttttaaatta   2640
aaaatgaagt tttaaatcaa tctaaagtat atatgagtaa acttggtctg acagttacca   2700
atgcttaatc agtgaggcac ctatctcagc gatctgtcta tttcgttcat ccatagttgc   2760
ctgactcccc gtcgtgtaga taactacgat acgggagggc ttaccatctg gccccagtgc   2820
tgcaatgata ccgcgagacc cacgctcacc ggctccagat ttatcagcaa taaaccagcc   2880
agccggaagg gccgagcgca gaagtggtcc tgcaacttta tccgcctcca tccagtctat   2940
taattgttgc cgggaagcta gagtaagtag ttcgccagtt aatagtttgc gcaacgttgt   3000
tgccattgct acaggcatcg tggtgtcacg ctcgtcgttt ggtatggctt cattcagctc   3060
cggttcccaa cgatcaaggc gagttacatg atccccatg  ttgtgcaaaa aagcggttag   3120
ctccttcggt cctccgatcg ttgtcagaag taagttggcc gcagtgttat cactcatggt   3180
tatggcagca ctgcataatt ctcttactgt catgccatcc gtaagatgct tttctgtgac   3240
tggtgagtac tcaaccaagt cattctgaga atagtgtatg cggcgaccga gttgctcttg   3300
cccggcgtca atacgggata ataccgcgcc acatagcaga actttaaaag tgctcatcat   3360
tggaaaacgt tcttcggggc gaaaactctc aaggatctta ccgctgttga gatccagttc   3420
gatgtaaccc actcgtgcac ccaactgatc ttcagcatct tttactttca ccagcgtttc   3480
tgggtgagca aaaacaggaa ggcaaaatgc cgcaaaaaag gaataagggg cgacacggaa   3540
atgttgaata ctcatactct ccttttttca atattattga agcatttatc agggttattg   3600
tctcatgagc ggatacatat ttgaatgtat ttagaaaaat aaacaaatag ggttccgcg   3660 cacatttccc cgaaaagtgc cacctgacgt ctaagaaacc attattatca tgacattaac   3720
ctataaaaat aggcgtatca cgaggcccct tcgtc                             3755
```

<210> SEQ ID NO 5
<211> LENGTH: 13
<212> TYPE: DNA
<213> ORGANISM: Artificial
<220> FEATURE:
<223> OTHER INFORMATION: First Sfi 1 syntehtic restriction site added

<400> SEQUENCE: 5
ggcccaggcg gcc                                                      13

<210> SEQ ID NO 6
<211> LENGTH: 13
<212> TYPE: DNA
<213> ORGANISM: Artificial

```
<220> FEATURE:
<223> OTHER INFORMATION: Second Sfi1 synthetic restriction site added

<400> SEQUENCE: 6
ggcctcaggg gcc                                                            13

<210> SEQ ID NO 7
<211> LENGTH: 11
<212> TYPE: DNA
<213> ORGANISM: Artificial
<220> FEATURE:
<223> OTHER INFORMATION: synthetic AccB7 I restriction site
<220> FEATURE:
<221> NAME/KEY: misc_feature
<222> LOCATION: (3)..(7)
<223> OTHER INFORMATION: n= a, c, t or g
<220> FEATURE:
<221> NAME/KEY: misc_feature
<222> LOCATION: (8)..(8)
<223> OTHER INFORMATION: n= a, c, t or g

<400> SEQUENCE: 7
ccannnnntg g                                                              11

<210> SEQ ID NO 8
<211> LENGTH: 11
<212> TYPE: DNA
<213> ORGANISM: Artificial
<220> FEATURE:
<223> OTHER INFORMATION: synthetic Bgl I restriction site
<220> FEATURE:
<221> NAME/KEY: misc_feature
<222> LOCATION: (4)..(8)
<220> FEATURE:
<221> NAME/KEY: misc_feature
<222> LOCATION: (4)..(8)
<223> OTHER INFORMATION: n is a, c, g, or t

<400> SEQUENCE: 8
gccnnnnngg c                                                              11

<210> SEQ ID NO 9
<211> LENGTH: 10
<212> TYPE: DNA
<213> ORGANISM: Artificial
<220> FEATURE:
<223> OTHER INFORMATION: Synthetic BsrBR I restriction site
<220> FEATURE:
<221> NAME/KEY: misc_feature
<222> LOCATION: (4)..(7)
<223> OTHER INFORMATION: n= a, t, c or g

<400> SEQUENCE: 9 gatnnnnatc                                                                10

<210> SEQ ID NO 10
<211> LENGTH: 12
<212> TYPE: DNA
<213> ORGANISM: Artificial
<220> FEATURE:
<223> OTHER INFORMATION: Synthetic BST XI restriction site
<220> FEATURE:
<221> NAME/KEY: misc_feature
<222> LOCATION: (4)..(9)
<223> OTHER INFORMATION: n= a, t, c or g

<400> SEQUENCE: 10
ccannnnnnt gg                                                             12
```

```
<210> SEQ ID NO 11
<211> LENGTH: 11
<212> TYPE: DNA
<213> ORGANISM: Artificial
<220> FEATURE:
<223> OTHER INFORMATION: Synthetic Ecl HKI restriction site
<220> FEATURE:
<221> NAME/KEY: misc_feature
<222> LOCATION: (4)..(8)
<223> OTHER INFORMATION: n= a, t, c or g

<400> SEQUENCE: 11
gacnnnnngt c                                                          11

<210> SEQ ID NO 12
<211> LENGTH: 15
<212> TYPE: DNA
<213> ORGANISM: Artificial
<220> FEATURE:
<223> OTHER INFORMATION: Synthetic I-Ppo I

<400> SEQUENCE: 12
ctctcttaag gtagc                                                      15

<210> SEQ ID NO 13
<211> LENGTH: 13
<212> TYPE: DNA
<213> ORGANISM: Artificial
<220> FEATURE:
<223> OTHER INFORMATION: Synthetic Sfi I restriction site
<220> FEATURE:
<221> NAME/KEY: misc_feature
<222> LOCATION: (5)..(9)
<223> OTHER INFORMATION: n= a, t, c or g

<400> SEQUENCE: 13
ggccnnnnng gcc                                                        13

<210> SEQ ID NO 14
<211> LENGTH: 10
<212> TYPE: DNA
<213> ORGANISM: Artificial
<220> FEATURE:
<223> OTHER INFORMATION: Synthetic Xmn I restriction site
<220> FEATURE:
<221> NAME/KEY: misc_feature
<222> LOCATION: (4)..(7)
<223> OTHER INFORMATION: n= a, t, c or g

<400> SEQUENCE: 14 gaannnnttc                                                            10

<210> SEQ ID NO 15
<211> LENGTH: 13
<212> TYPE: DNA
<213> ORGANISM: Artificial
<220> FEATURE:
<223> OTHER INFORMATION: Synthetic Kozak sequence

<400> SEQUENCE: 15
gccgccacca tgg                                                        13

<210> SEQ ID NO 16
<211> LENGTH: 16
<212> TYPE: PRT
<213> ORGANISM: Artificial
<220> FEATURE:
<223> OTHER INFORMATION: Synthetic flexible linker sequence
```

```
<400> SEQUENCE: 16

Asp Gly Gly Gly Ser Gly Gly Gly Ser Gly Gly Gly Gly Ser Ser
1               5                   10                  15

<210> SEQ ID NO 17
<211> LENGTH: 9
<212> TYPE: PRT
<213> ORGANISM: Artificial
<220> FEATURE:
<223> OTHER INFORMATION: Synthetic LCDR3 sequence

<400> SEQUENCE: 17

Leu Glu Phe Asp Glu His Pro Leu Thr
1               5

<210> SEQ ID NO 18
<211> LENGTH: 8
<212> TYPE: PRT
<213> ORGANISM: Artificial
<220> FEATURE:
<223> OTHER INFORMATION: Synthetic LCDR 3 sequence

<400> SEQUENCE: 18

Leu Glu Phe Ser Leu Ser Arg Ser
1               5

<210> SEQ ID NO 19
<211> LENGTH: 9
<212> TYPE: PRT
<213> ORGANISM: Artificial
<220> FEATURE:
<223> OTHER INFORMATION: Synthetic LCDR 3 sequence

<400> SEQUENCE: 19

Leu Gln Phe Asp Ser His Pro Leu Thr
1               5

<210> SEQ ID NO 20
<211> LENGTH: 9
<212> TYPE: PRT
<213> ORGANISM: Artificial
<220> FEATURE:
<223> OTHER INFORMATION: Synthetic LCDR 3 sequence

<400> SEQUENCE: 20

Leu Gln Phe Asp Asn His Pro Leu Thr
1               5

<210> SEQ ID NO 21
<211> LENGTH: 9
<212> TYPE: PRT
<213> ORGANISM: Artificial
<220> FEATURE:
<223> OTHER INFORMATION: Synthetic LCDR 3 sequence
<220> FEATURE:
<221> NAME/KEY: UNSURE
<222> LOCATION: (8)..(8)
<223> OTHER INFORMATION: Xaa can be any naturally occurring amino acid

<400> SEQUENCE: 21

Leu Gln Tyr Asp Ala His Pro Xaa Thr
1               5

<210> SEQ ID NO 22
<211> LENGTH: 9
<212> TYPE: PRT
<213> ORGANISM: Artificial
```

```
<220> FEATURE:
<223> OTHER INFORMATION: Synthetic LCDR 3 sequence

<400> SEQUENCE: 22

Leu Gln Phe Asp Val His Pro Leu Thr
1               5

<210> SEQ ID NO 23
<211> LENGTH: 9
<212> TYPE: PRT
<213> ORGANISM: Artificial
<220> FEATURE:
<223> OTHER INFORMATION: Synthetic LCDR 3 sequence

<400> SEQUENCE: 23

Leu Gln Tyr Asp Ala His Pro Leu Thr
1               5

<210> SEQ ID NO 24
<211> LENGTH: 9
<212> TYPE: PRT
<213> ORGANISM: Artificial
<220> FEATURE:
<223> OTHER INFORMATION: Synthetic LCDR 3 sequence
<220> FEATURE:
<221> NAME/KEY: UNSURE
<222> LOCATION: (1)..(5)
<223> OTHER INFORMATION: Xaa= ANY AMINO ACID

<400> SEQUENCE: 24

Xaa Xaa Phe Xaa Xaa His Pro Leu Thr
1               5

<210> SEQ ID NO 25
<211> LENGTH: 9
<212> TYPE: PRT
<213> ORGANISM: Artificial
<220> FEATURE:
<223> OTHER INFORMATION: Synthetic LCDR 3 sequence

<400> SEQUENCE: 25

Leu Gln Phe Asp Ala His Pro Leu Thr
1               5

<210> SEQ ID NO 26
<211> LENGTH: 9
<212> TYPE: PRT
<213> ORGANISM: Artificial
<220> FEATURE:
<223> OTHER INFORMATION: Synthetic LCDR 3 sequence

<400> SEQUENCE: 26

Leu Gln Phe Asp Ser His Pro Leu Thr
1               5

<210> SEQ ID NO 27
<211> LENGTH: 9
<212> TYPE: PRT
<213> ORGANISM: Artificial
<220> FEATURE:
<223> OTHER INFORMATION: Synthetic LCDR 3 sequence

<400> SEQUENCE: 27

Leu Gln Tyr Asp Ala His Pro Leu Thr
1               5

<210> SEQ ID NO 28
```

```
<211> LENGTH: 9
<212> TYPE: PRT
<213> ORGANISM: Artificial
<220> FEATURE:
<223> OTHER INFORMATION: Synthetic LCDR 3 sequence
<220> FEATURE:
<221> NAME/KEY: UNSURE
<222> LOCATION: (1)..(5)
<223> OTHER INFORMATION: Xaa + ANY AMINO ACID

<400> SEQUENCE: 28

Xaa Xaa Phe Asp Xaa His Pro Leu Thr
1               5

<210> SEQ ID NO 29
<211> LENGTH: 9
<212> TYPE: PRT
<213> ORGANISM: Artificial
<220> FEATURE:
<223> OTHER INFORMATION: Synthetic LCDR 3 sequence

<400> SEQUENCE: 29

Leu Glu Leu Asp Glu His Pro Leu Thr
1               5

<210> SEQ ID NO 30
<211> LENGTH: 9
<212> TYPE: PRT
<213> ORGANISM: Artificial
<220> FEATURE:
<223> OTHER INFORMATION: Synthetic LCDR 3 sequence

<400> SEQUENCE: 30

Leu Gln Phe Asp Glu His Pro Leu Thr
1               5

<210> SEQ ID NO 31
<211> LENGTH: 9
<212> TYPE: PRT
<213> ORGANISM: Artificial
<220> FEATURE:
<223> OTHER INFORMATION: Synthetic LCDR 3 sequence

<400> SEQUENCE: 31

Leu Gln Tyr Asp Ala His Pro Leu Thr
1               5

<210> SEQ ID NO 32
<211> LENGTH: 9
<212> TYPE: PRT
<213> ORGANISM: Artificial
<220> FEATURE:
<223> OTHER INFORMATION: Synthetic HCDR 3 sequence

<400> SEQUENCE: 32

Gly Gly Asp Ile Thr Thr Gly Phe Asp
1               5

<210> SEQ ID NO 33
<211> LENGTH: 10
<212> TYPE: PRT
<213> ORGANISM: Artificial
<220> FEATURE:
<223> OTHER INFORMATION: Synthetic HCDR 3 sequence

<400> SEQUENCE: 33

Gly Gly Asp Ile Leu Val Ser Leu Asp Val
1               5                   10
```

```
<210> SEQ ID NO 34
<211> LENGTH: 10
<212> TYPE: PRT
<213> ORGANISM: Artificial
<220> FEATURE:
<223> OTHER INFORMATION: Synthetic HCDR 3 sequence

<400> SEQUENCE: 34

Gly Gly Asp Ile Leu Val Gly Leu Asp Tyr
1               5                   10

<210> SEQ ID NO 35
<211> LENGTH: 10
<212> TYPE: PRT
<213> ORGANISM: Artificial
<220> FEATURE:
<223> OTHER INFORMATION: Synthetic HCDR 3 sequence

<400> SEQUENCE: 35

Gly Gly Asp Ile Arg Glu Gly Leu Arg Tyr
1               5                   10

<210> SEQ ID NO 36
<211> LENGTH: 10
<212> TYPE: PRT
<213> ORGANISM: Artificial
<220> FEATURE:
<223> OTHER INFORMATION: Synthetic HCDR 3 sequence

<400> SEQUENCE: 36

Gly Gly Asp Ile Val Val Gly Leu Asp His
1               5                   10

<210> SEQ ID NO 37
<211> LENGTH: 10
<212> TYPE: PRT
<213> ORGANISM: Artificial
<220> FEATURE:
<223> OTHER INFORMATION: Synthetic HCDR 3 sequence

<400> SEQUENCE: 37

Gly Gly Asp Ile Arg Val Ser Leu Asp His
1               5                   10

<210> SEQ ID NO 38
<211> LENGTH: 10
<212> TYPE: PRT
<213> ORGANISM: Artificial
<220> FEATURE:
<223> OTHER INFORMATION: Synthetic HCDR 3 sequence

<400> SEQUENCE: 38

Gly Gly Asp Ile Lys Val Gly Leu Asp Leu
1               5                   10

<210> SEQ ID NO 39
<211> LENGTH: 10
<212> TYPE: PRT
<213> ORGANISM: Artificial
<220> FEATURE:
<223> OTHER INFORMATION: Synthetic HCDR 3 sequence

<400> SEQUENCE: 39

Gly Gly Asp Ile Arg Val Met Leu Asp Leu
1               5                   10
```

```
<210> SEQ ID NO 40
<211> LENGTH: 10
<212> TYPE: PRT
<213> ORGANISM: Artificial
<220> FEATURE:
<223> OTHER INFORMATION: Synthetic HCDR 3 sequence

<400> SEQUENCE: 40

Gly Gly Asp Ile Lys Val Ser Leu Asp His
1               5                   10

<210> SEQ ID NO 41
<211> LENGTH: 10
<212> TYPE: PRT
<213> ORGANISM: Artificial
<220> FEATURE:
<223> OTHER INFORMATION: Synthetic HCDR 3 sequence

<400> SEQUENCE: 41

Gly Gly Asp Ile Lys Val Ser Leu Asp His
1               5                   10

<210> SEQ ID NO 42
<211> LENGTH: 10
<212> TYPE: PRT
<213> ORGANISM: Artificial
<220> FEATURE:
<223> OTHER INFORMATION: Synthetic HCDR 3 sequence

<400> SEQUENCE: 42

Gly Gly Asp Ile Arg Val Gly Leu Asp Val
1               5                   10

<210> SEQ ID NO 43
<211> LENGTH: 10
<212> TYPE: PRT
<213> ORGANISM: Artificial
<220> FEATURE:
<223> OTHER INFORMATION: Synthetic HCDR 3 sequence

<400> SEQUENCE: 43

Gly Gly Asp Ile Ile Ile Ser Leu Asp Trp
1               5                   10

<210> SEQ ID NO 44
<211> LENGTH: 10
<212> TYPE: PRT
<213> ORGANISM: Artificial
<220> FEATURE:
<223> OTHER INFORMATION: Synthetic HCDR 3 sequence

<400> SEQUENCE: 44

Gly Gly Asp Ile Lys Val Gly Leu Asp Asn
1               5                   10

<210> SEQ ID NO 45
<211> LENGTH: 10
<212> TYPE: PRT
<213> ORGANISM: Artificial
<220> FEATURE:
<223> OTHER INFORMATION: Synthetic HCDR 3 sequence

<400> SEQUENCE: 45

Gly Gly Asp Ile Lys Val Ser Leu Asp Arg
1               5                   10
```

```
<210> SEQ ID NO 46
<211> LENGTH: 10
<212> TYPE: PRT
<213> ORGANISM: Artificial
<220> FEATURE:
<223> OTHER INFORMATION: Synthetic HCDR 3 sequence

<400> SEQUENCE: 46

Gly Gly Asp Ile Thr Leu Gly Leu Asp Val
1               5                   10

<210> SEQ ID NO 47
<211> LENGTH: 10
<212> TYPE: PRT
<213> ORGANISM: Artificial
<220> FEATURE:
<223> OTHER INFORMATION: Synthetic HCDR 3 sequence

<400> SEQUENCE: 47

Asp Asp Asp Ile Lys Val Ser Leu Asp Gln
1               5                   10

<210> SEQ ID NO 48
<211> LENGTH: 10
<212> TYPE: PRT
<213> ORGANISM: Artificial
<220> FEATURE:
<223> OTHER INFORMATION: Synthetic HCDR 3 sequence

<400> SEQUENCE: 48

Gly Gly Asp Ile Arg Val Ser Leu Asp Phe
1               5                   10

<210> SEQ ID NO 49
<211> LENGTH: 10
<212> TYPE: PRT
<213> ORGANISM: Artificial
<220> FEATURE:
<223> OTHER INFORMATION: Synthetic HCDR 3 sequence

<400> SEQUENCE: 49

Gly Gly Asp Ile Arg Val Met Leu Asp Val
1               5                   10

<210> SEQ ID NO 50
<211> LENGTH: 10
<212> TYPE: PRT
<213> ORGANISM: Artificial
<220> FEATURE:
<223> OTHER INFORMATION: Synthetic HCDR 3 sequence

<400> SEQUENCE: 50

Gly Gly Asp Ile Leu Asp Ser Leu His Phe
1               5                   10

<210> SEQ ID NO 51
<211> LENGTH: 69
<212> TYPE: PRT
<213> ORGANISM: Bacteriophage M13

<400> SEQUENCE: 51

Glu Gly Gly Gly Ser Gly Gly Gly Ser Gly Asp Phe Asp Tyr
1               5                   10                  15

Glu Lys Met Ala Asn Ala Asn Lys Gly Ala Met Thr Glu Asn Ala Asp
            20                  25                  30

Glu Asn Ala Leu Gln Ser Asp Ala Lys Gly Lys Leu Asp Ser Val Ala
```

-continued

```
             35                  40                  45
Thr Asp Tyr Gly Ala Ala Ile Asp Gly Phe Ile Gly Asp Val Ser Gly
    50                  55                  60

Leu Ala Asn Gly Asn
65
```

COMPATIBLE DISPLAY VECTOR SYSTEMS

CROSS REFERENCE TO RELATED APPLICATIONS

This application is a continuation application of U.S. patent application Ser. No. 12/566,854, filed Sep. 25, 2009, now issued as U.S. Pat. No. 8,313,942, which claims priority to U.S. Provisional Patent Application No. 61/100,432, filed Sep. 26, 2008, both of which are incorporated by reference herein in their entirety.

FIELD OF THE INVENTION

The present invention generally relates to compositions comprising polynucleotide vectors used for the expression and display of polypeptides, and to methods in which such compositions are used.

BACKGROUND

Protein therapeutics are an important part of drug discovery. High-throughput screening of large libraries of polynucleotides encoding protein variants, which may include antigen binding polypeptides or fragments thereof, allows efficient discovery or optimization of protein therapeutics for desirable properties such as binding affinity, avidity, stability and specificity. Typical tools used for high-throughput screen include phage and ribosome display techniques.

Therapeutic antigen binding polypeptides or fragments are particularly attractive because of their high affinity and specificity to the antigen and because of their relatively high stability in vitro and in vivo. Antibodies are made of two heavy and two light chains, which contain the variable regions at their N-terminus and are linked by disulfide bridges. Single-chain antibodies in particular have been engineered by linking fragments of the variable heavy and light chain regions (ScFv) into a single polypeptide.

Typical procedures for making ScFv generally involve amplification of gene regions that encode the variable regions of the antibodies, assembly of an ScFv genetic sequence and expression of the ScFv polypeptide sequence in host cells. The host cells are screened using a target polypeptide of interest to identify those cells that express a ScFv polypeptide that binds to this target polypeptide. The host cells can subsequently be analyzed for the polynucleotide coding sequence encoding the expressed ScFv. The most commonly used techniques to identify single-chain antibodies that bind specific polypeptides is by phage display and variations thereof (see Hoogenboom et al., 1998). Generally, phage display methods involve the insertion of random heterologous polynucleotides into a phage genome such that they direct a bacterial host to express peptide libraries fused to phage coat proteins (e.g., filamentous phage pIII, pVI or pVIII). Libraries of up to $10^{10}$ individual members can be routinely prepared and screened in this way. Incorporation of the ScFv sequences into the mature phage coat sequence results in the ScFv antibodies encoded by the heterologous polynucleotide sequence being displayed on the exterior surface of the phage. By immobilizing a relevant polypeptide target (or targets) of interest to a surface, a phage that expresses and displays an ScFv that binds to one of those targets on the surface will remain bound while others are removed by washing.

SUMMARY OF THE INVENTION

The present invention provides a polynucleotide vector system that is used during ribosome display and can be used to facilitate transfer of pools of polynucleotides that encode antigen binding proteins of interest between the ribosome display polynucleotide of the invention and a phage display polynucleotide. In particular, the present invention provides compatible expression and display systems that allow seamless conversion of pools of polynucleotides encoding antigen binding proteins using a restriction enzyme digestion and ligation strategy.

In one aspect, the present invention provides a polynucleotide comprising a nucleotide sequence, the polynucleotide comprising from 5' to 3': a promoter sequence, a sequence capable of forming a stem-loop structure, a first and second Sfi I site, a sequence encoding an amino acid sequence that lacks a stop codon, and an origin of replication.

In some embodiments, ribosome display technology allows efficient optimization of protein therapeutics, including therapeutic antibodies, for properties such as affinity, stability and specificity. Ribosome display is an in vitro display technology that is not limited in library size by bacterial transformation efficiency, meaning that vast libraries (e.g., with more than $10^{12}$ members) can be generated.

In some embodiments the polynucleotide comprises a first and second Sfi I restriction sites that are not compatible with each other. In some embodiments the first Sfi I restriction site comprises SEQ ID NO. 5, or it's compliment. In some embodiments the second Sfi I restriction site comprises SEQ ID NO. 6, or it's compliment. In one or more embodiments the polynucleotide of the invention further comprises a nucleic acid sequence that encodes a tag sequence 3' to the first Sfi I sequence. In some embodiments the tag sequence is selected from the group consisting of a flag tag, a c-myc tag, a histidine tag, a GST tag, a green fluorescent protein tag, an HA tag, and E-tag, a Strep tag, a Strep tag II and a YoI 1/34 tag. In some embodiments the tag sequence is a flag tag. In some embodiments the polynucleotide of the invention provides the nucleotide sequence that encodes the amino acid sequence that lacks a stop codon encodes is at least 20 amino acids. In some embodiments, the amino acid sequence that lacks a stop codon encodes 69 amino acids. In some embodiments, the amino acid sequence that lacks a stop codon is selected from the group consisting of: the constant region of immunoglobulin kappa chain (Ck), gene III of filamentous phage M13, and the CH3 domain of human IgM. In some embodiments the amino acid sequence that lacks a stop codon is derived from gene III of filamentous phage M13. In some embodiments, the amino acid sequence that lacks a stop codon encodes 69 amino acids in length.

In one or more embodiments the polynucleotide of the invention comprises a promoter selected from T7, SP6 or T3. In some embodiments the promoter is a T7 promoter. In one or more embodiments the polynucleotide of the invention comprises a prokaryotic origin of replication.

In one or more embodiments the polynucleotide of the invention that forms a stem loop structures are 5' and 3' stem loop structures.

In one or more embodiments the polynucleotide of the invention further comprises a polynucleotide sequence 3' to the promoter sequence that encodes a ribosome binding site.

In one or more embodiments, the polynucleotide of the invention comprises SEQ ID NO. 3 (pWRIL-3 sequence).

In one or more embodiments, the polynucleotide of the invention further comprises a eukaryotic origin of replication. In one or more embodiments, the polynucleotide of the invention provides that the stem-loop structure is a 3' stem loop structure.

In one or more embodiments, the polynucleotide of the invention further comprises a sequence 3' to the promoter sequence that encodes a translation enhancer. In some embodiments, the translational enhancer is selected from the group consisting of: *X. laevis* β-globin gene translational enhancer, untranslated leader sequences from tobacco mosaic virus, 5' untranslated region from alfalfa mosaic virus RNA 4, black beetle virus (Nodavirus) RNA 2, turnip mosaic virus coat protein mRNAs, and brome mosaic virus coat protein mRNAs. In some embodiments, the polynucleotide of the invention provides that the translational enhancer is the *X. laevis* β-globin gene translational enhancer.

In one or more embodiments, the polynucleotide of the invention comprises SEQ ID NO:4 (pWRIL-4 sequence).

The present invention also provides for cells containing one or more of the polynucleotides of the invention, in particular, as described in the various embodiments above.

In another aspect, the present invention provides a method of generating a ribosome display library, the method comprising the steps of: (a) replicating a polynucleotide of any of the polynucleotides described in the various embodiments above to create a plurality of replication products of the polynucleotide (b) digesting the replication products of step (a) with Sfi I restriction enzyme; (c) ligating the population of SfiI digested polynucleotides of step (b) with a plurality of polynucleotides each comprising in 5' to 3' direction: a first Sfi site, a polynucleotide encoding an antigen binding polypeptide and a second Sfi site, wherein the first Sfi I site is compatible with the first Sfi I step (b) and the second Sfi I site is compatible with the second Sfi I site of step (b); and (d) recovering the ligation product of step (c).

In some embodiments, the method of the invention provides that the first and second Sfi I restriction sites are not compatible with each other. In some embodiments, the method of the invention provides that the first Sfi I restriction site comprises SEQ ID NO. 5, or it's compliment. In some embodiments, the method of the invention provides that the second Sfi I restriction site comprises SEQ ID NO. 6, or it's compliment.

In some embodiments, the method of the invention provides that the polynucleotide of (a) is a ribosome display polynucleotide and comprises SEQ ID NO: 3 (pWRIL-3 sequence).

In some embodiments, the method of the invention provides that the polynucleotide of (a) is a ribosome display polynucleotide and comprises SEQ ID NO: 4 (pWRIL-4 sequence).

In one or more embodiments, the method of the invention provides that the antigen binding polypeptide is selected from the group consisting of: a peptide, a chimeric antibody, a humanized antibody, a human antibody, a single chain antibody, a tetrameric antibody, a tetravalent antibody, a multispecific antibody, a domain-specific antibody, a domain-deleted antibody, a fusion protein, an ScFc fusion protein, an Fab fragment, an Fab' fragment, an F(ab')2 fragment, an Fv fragment, a single-chain Fv (ScFv) fragment, an Fd fragment, a single domain antibody, a dAb fragment, a small modular immunopharmaceutical (SMIP), a shark variable IgNAR domain, a CDR3 peptide, a constrained FR3-CDR3-FR4 peptide, a nanobody, a bivalent nanobody and a minibody. In some embodiments, the method of the invention provides that the antigen binding polypeptide is a single-chain Fv (ScFv) antibody.

The present invention also provides a ribosome display library containing one or more of the polynucleotides of the invention, in particular, as described in the various embodiments above.

The present invention also provides for cells containing one or more of the polynucleotides generated by methods of the invention, in particular, as described in the various embodiments above.

In another aspect, the present invention provides a method of generating a ribosome display library comprising polynucleotides from a population of phage display polynucleotides each encoding an antigen binding polypeptide, the method comprising: (a) generating a population of phage display polynucleotides that encode an antigen binding polypeptide that specifically binds to a binding partner, each polynucleotide comprising in order from 5' to 3': a first Sfi I sequence, a polynucleotide that encodes the antigen binding polypeptide and a second Sfi I sequence; and (b) isolating the polynucleotide from step (a); (c) generating a plurality of polynucleotides by digesting the polynucleotides from step (b) with an Sfi I restriction enzyme; (d) replicating a polynucleotide of any of the polynucleotides described in the various embodiments above to create a plurality of replication products of the polynucleotide (e) digesting the plurality of replication products of step (d) with an Sfi I restriction enzyme; (f) ligating the population of Sfi I digested polynucleotides of step (b) with the plurality of polynucleotides of step (e) wherein the first Sfi I site of step (c) is compatible with the first Sfi I site of step (e) and the second Sfi I site of step (c) is compatible with the second Sfi I site of step (e); and (g) recovering the ligation products of step (c).

In some embodiments, the method of the invention provides that the generation step (b) comprises isolated polynucleotides that undergo error prone PCR.

In some embodiments, the method of the invention provides that the generation step (b) comprises isolated polynucleotides that undergo targeted mutagenesis.

In some embodiments, the method of the invention provides that the first and second Sfi I restriction sites are not compatible with each other. In some embodiments, the method of the invention provides that the first Sfi I restriction site comprises SEQ ID NO. 5, or it's compliment.

In some embodiments, the method of the invention provides that the second Sfi I restriction site comprises SEQ ID NO. 6, or it's compliment.

In some embodiments, the method of the invention provides that the polynucleotide in (d) is a ribosome display polynucleotide and comprises SEQ ID NO: 3 (pWRIL-3 sequence).

In some embodiments, the method of the invention provides that the polynucleotide in (d) is a ribosome display polynucleotide and comprises SEQ ID NO: 4 (pWRIL-4 sequence).

In some embodiments, the method of the invention provides that phage display polynucleotide comprises SEQ ID NO. 1 (pWRIL-1).

In some embodiments, the method of the invention provides that the phage display polynucleotide comprises SEQ ID NO. 2 (pWRIL-2).

In some embodiments, the method of the invention provides that the antigen binding polypeptide is selected from the group consisting of: a peptide, a chimeric antibody, a humanized antibody, a human antibody, a single chain antibody, a tetrameric antibody, a tetravalent antibody, a multispecific antibody, a domain-specific antibody, a domain-deleted antibody, a fusion protein, an ScFc fusion protein, an Fab fragment, an Fab' fragment, an F(ab')2 fragment, an Fv fragment, a single-chain Fv (ScFv) fragment, an Fd fragment, a single domain antibody, a dAb fragment, a small modular immunopharmaceutical (SMIP), a shark variable IgNAR domain, a CDR3 peptide, a constrained FR3-CDR3-FR4 peptide, a nanobody, a bivalent nanobody and a minibody. In some embodiments, the method of the invention provides that the antigen binding polypeptide is a single-chain Fv (ScFv) antibody.

The present invention also provides a ribosome display library constructed containing the polynucleotides of this aspect of the invention, in particular, as described in the various embodiments above.

The present invention also provides for cells containing the polynucleotides generated by methods of the invention, in particular, as described in the various embodiments above.

BRIEF DESCRIPTION OF THE SEQUENCES

Figure 1:
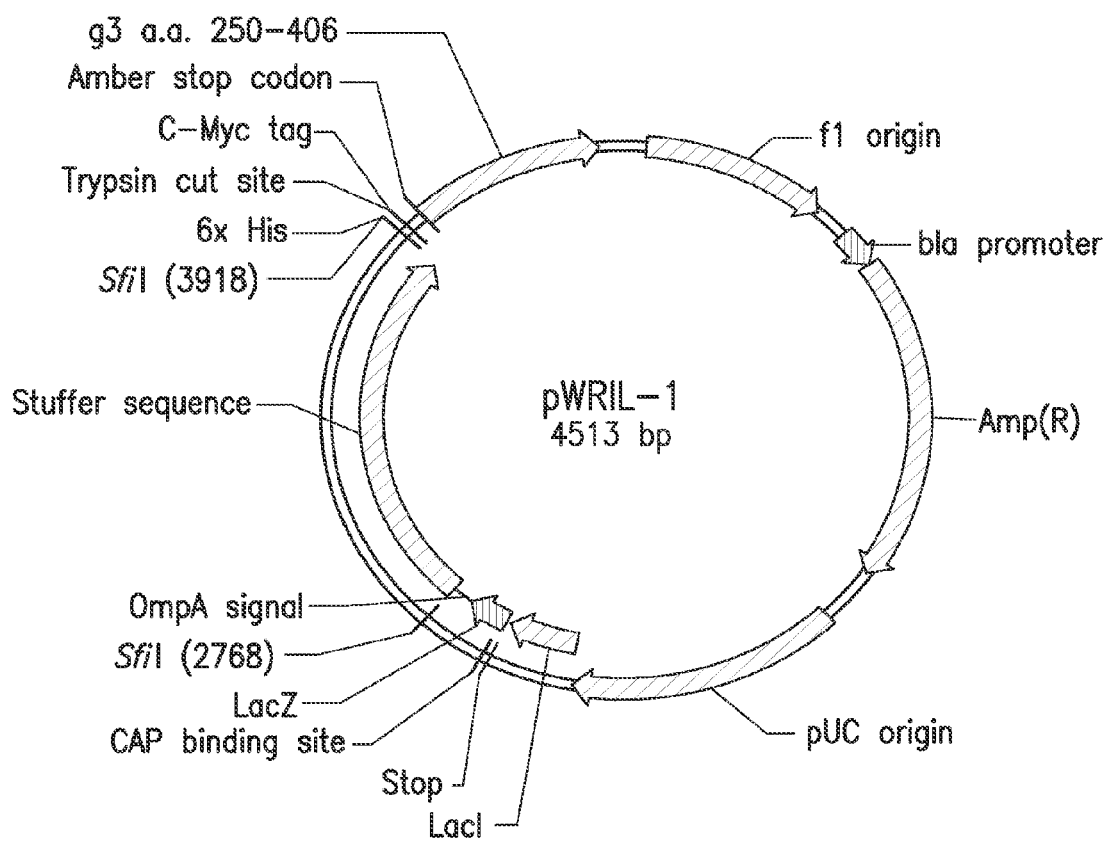
FIG. 1 illustrates the design map of an exemplary plasmid pWRIL-1.
Figure 2:
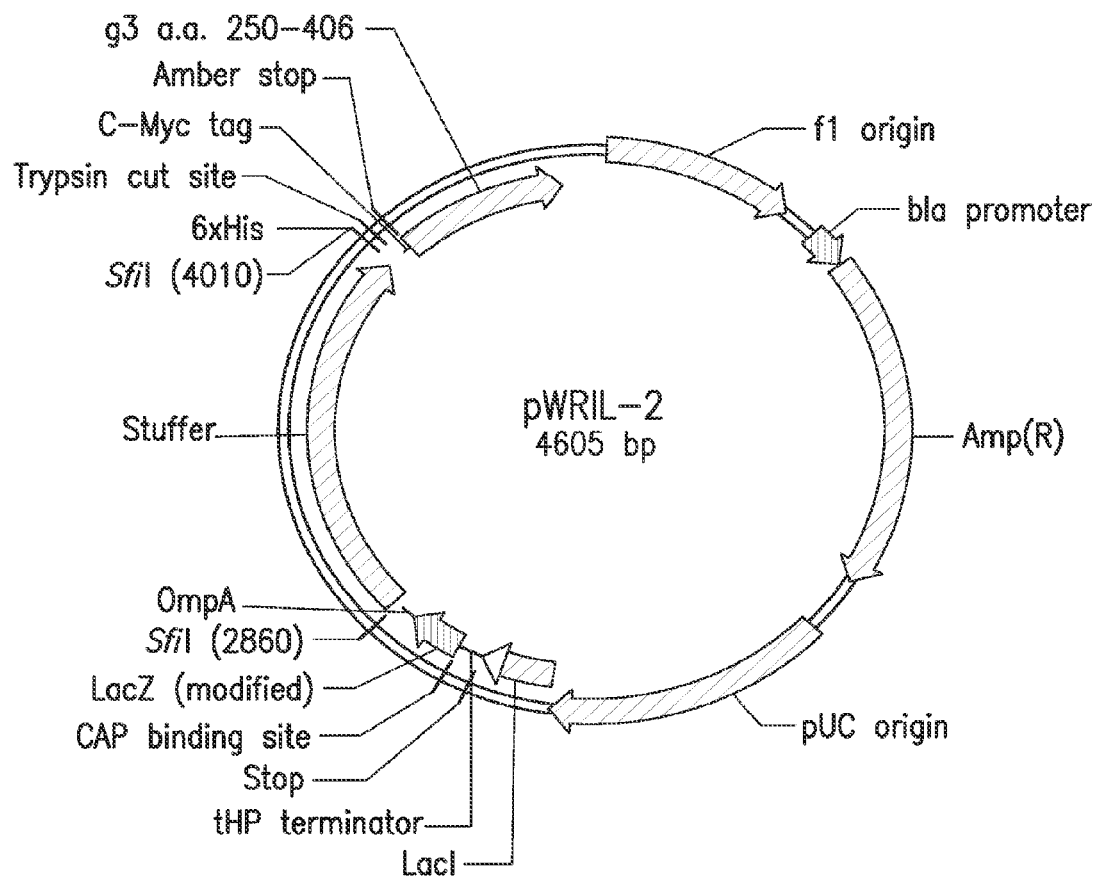
FIG. 2 illustrates the design map of an exemplary plasmid pWRIL-2.
Figure 3:
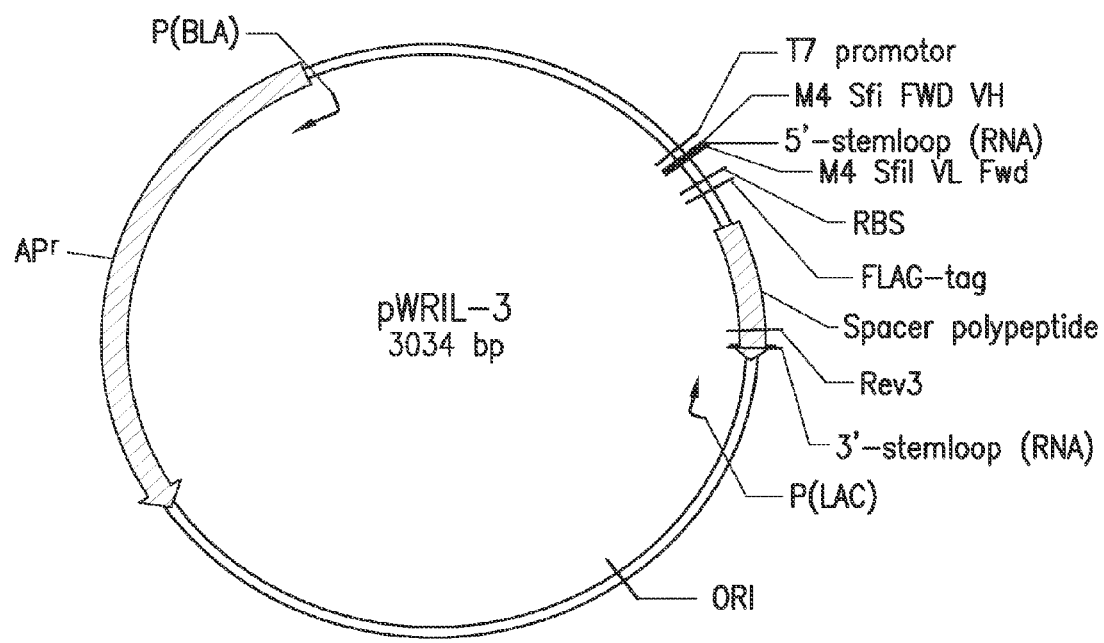
FIG. 3 illustrates the design maps of exemplary plasmid pWRIL-3.
Figure 4:
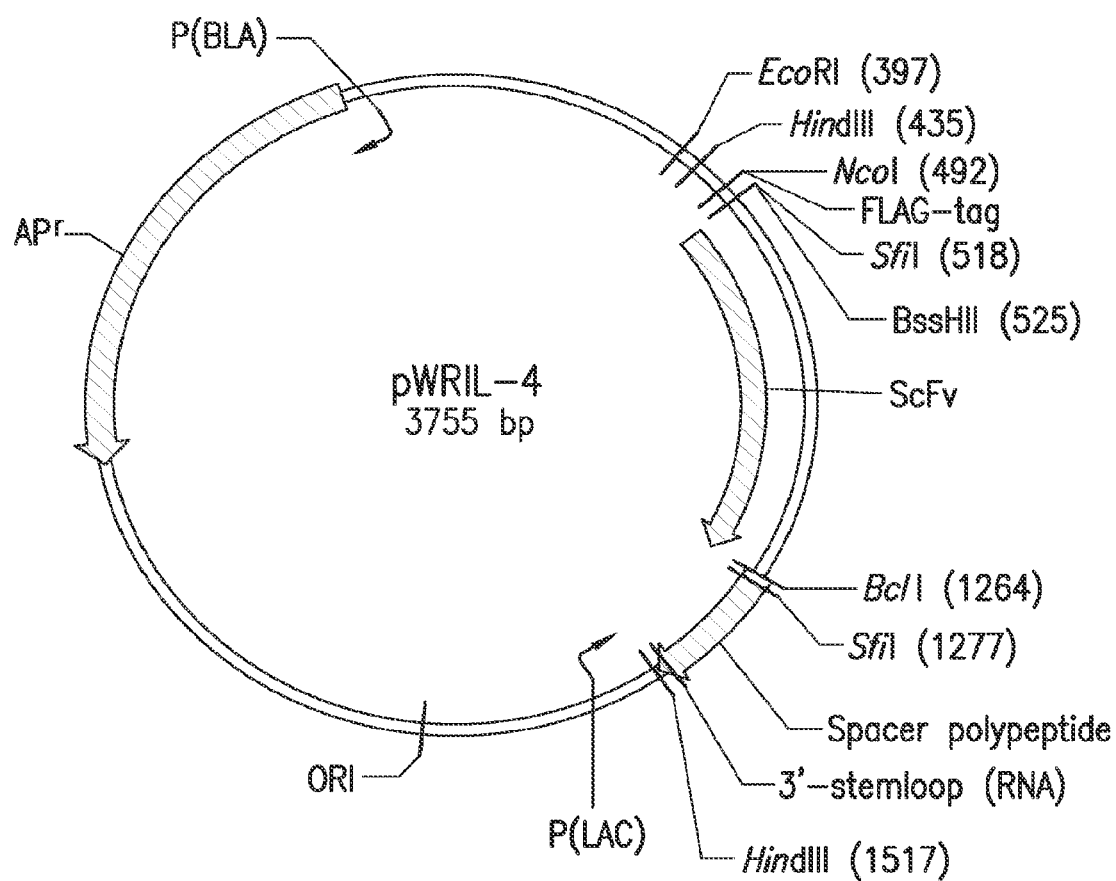
FIG. 4 illustrates the design maps of exemplary plasmid pWRIL-4.
Figure 5:
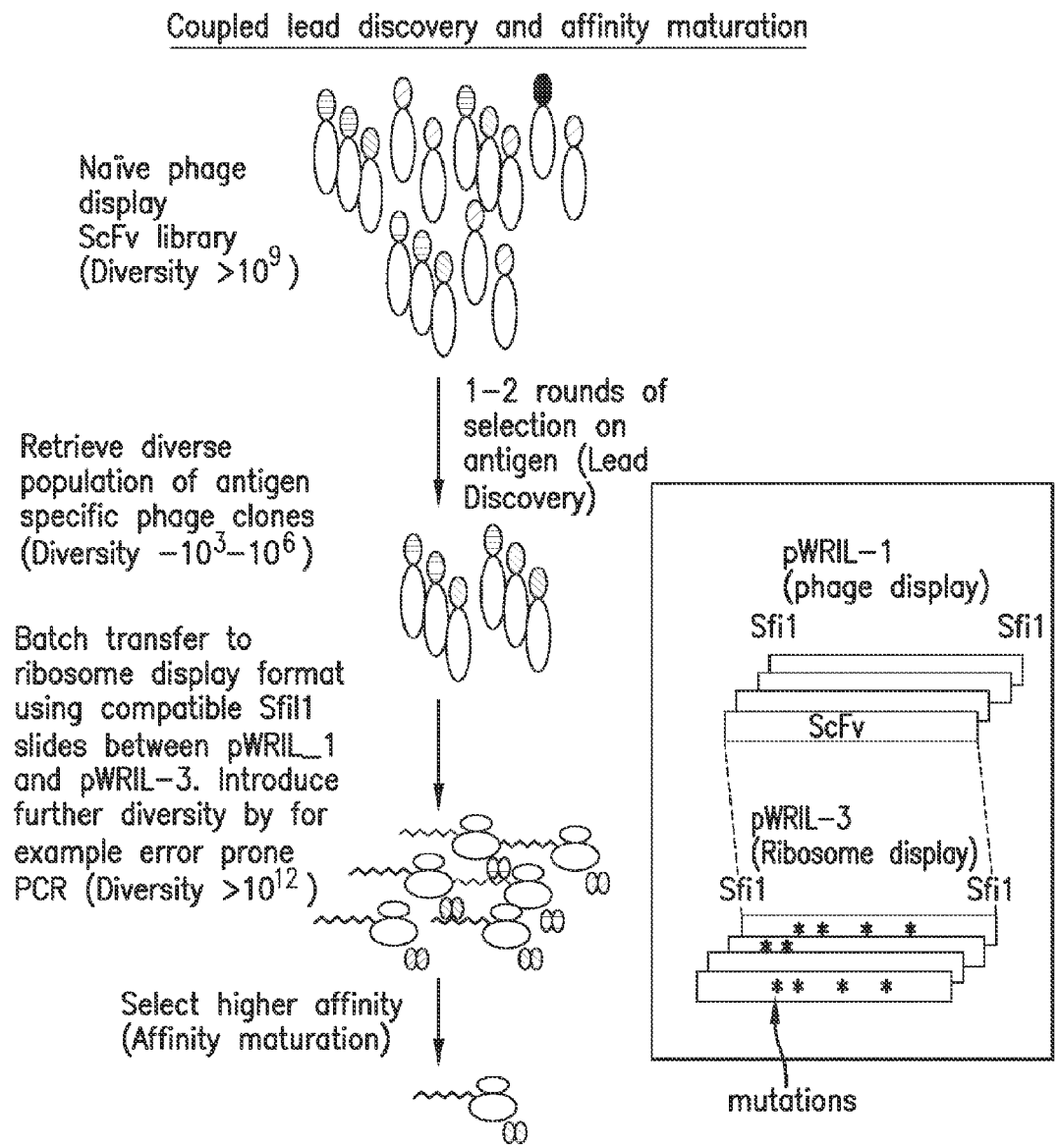
FIG. 5 represents a flow diagram showing coupled lead discovery and affinity maturation.

| SEQ ID NO: | DESCRIPTION OF THE SEQUENCES |
|---|---|
| 1 | pWRIL-1 |
| 2 | pWRIL-2 |
| 3 | pWRIL-3 |
| 4 | pWRIL-4 |
| 5 | First Sfi I site |
| 6 | Second Sfi I site |
| 7 | AccB71 restriction site |
| 8 | Bgl I restriction site |
| 9 | BsrBR I restriction site |
| 10 | Bst XI restriction site |
| 11 | EclHK I restriction site |
| 12 | I-Ppo I restriction site |
| 13 | Sfi I restriction site |
| 14 | Xmn I restriction site |
| 15 | Kozak Sequence |
| 16 | Flexible linker sequence |
| 17-31 | LCDR 3 sequences |
| 32-50 | HCDR3 sequences |
| 51 | Amino acids 249-318 of gene III of filamentous phage M13 |

DETAILED DESCRIPTION

The present invention provides polynucleotide vector systems containing restriction sites that allow rapid and transfer of a polynucleotide library that encode a pool of polypeptides between two vector systems for expression and display purposes. In particular, the present invention provides phage display polynucleotide vectors and ribosome display polynucleotide vectors that contain compatible restriction sites between the two vector systems that allow rapid assembly of high-diversity protein libraries and e transfer of polynucleotide sequences that encode polypeptides between libraries for affinity maturation or expression. The present invention also provides display libraries (e.g., phage display libraries and ribosome display libraries) constructed based on the polynucleotide vector systems of the invention and the methods of making and using the same.

Various aspects of the invention are described in detail in the following sections. The use of sections is not meant to limit the invention. Each section can apply to any aspect of the invention.

Definitions

For convenience, certain terms employed in the specification, examples, and appended claims are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

As used herein, the term "about" means within 20%, more preferably within 10% and most preferably within 5%.

The term "antigen-binding fragment" or "antigen-binding polypeptide" can be used interchangeably to refer to a polypeptide fragment of an immunoglobulin, antibody or antibody-like molecule, or fragment thereof, or other polypeptide molecule that binds antigen or competes with antibody that binds to the same antigenic site for antigen binding (i.e., specific binding). The term "antigen-binding polypeptide" includes intact molecules as well as fragments thereof, such as Fab, F(ab')$_2$, and Fv which are capable of binding the epitope. These antibody fragments retain some ability to selectively bind with its antigen or receptor and are defined as follows: (1) Fab, the fragment which contains a monovalent antigen-binding fragment of an antibody molecule can be produced by digestion of whole antibody with the enzyme papain to yield an intact light chain and a portion of one heavy chain; (2) Fab', the fragment of an antibody molecule can be obtained by treating whole antibody with pepsin, followed by reduction, to yield an intact light chain and a portion of the heavy chain; two Fab' fragments are obtained per antibody molecule; (3) (Fab')$_2$, the fragment of the antibody that can be obtained by treating whole antibody with the enzyme pepsin without subsequent reduction; F(ab')$_2$ is a dimer of two Fab' fragments held together by two disulfide bonds; (4) Fv, defined as a genetically engineered fragment containing the variable region of the light chain and the variable region of the heavy chain expressed as two chains; and (5) single chain antibody ("SCA"), defined as a genetically engineered molecule containing the variable region of the light chain, the variable region of the heavy chain, linked by a suitable polypeptide linker as a genetically fused single chain molecule. Methods of making these fragments are known in the art. (See for example, Harlow and Lane, *Antibodies: A Laboratory Manual*, Cold Spring Harbor Laboratory, New York (1988)).

As used herein, restriction sites are "compatible" if, once cleaved by appropriate restriction enzymes, can be ligated by a DNA ligase. In some embodiments, the compatible restriction sites include those double-stranded sequences that, once cleaved by appropriate restriction enzymes, generate "sticky ends" with complementary overhang sequences that can be joined by a DNA ligase.

As used herein, a "heterologous nucleotide sequence" refers to a nucleotide sequence that is added to a nucleotide sequence of the present invention by recombinant methods to form a nucleic acid which is not naturally formed in nature. Such nucleic acids can encode chimeric and/or fusion proteins/polypeptides. Thus the heterologous nucleotide sequence can encode peptides/ proteins that contain regulatory and/or structural properties.

A "host cell" is intended to include any individual cell or cell culture that can be or has been a recipient for vectors or for the incorporation of exogenous nucleic acid molecules, polynucleotides, and/or proteins. It also is intended to include progeny of a single cell. The progeny may not necessarily be completely identical (in morphology or in genomic or total DNA complement) to the original parent cell due to natural, accidental, or deliberate mutation. The cells may be prokaryotic or eukaryotic, and include but are not limited to bacterial cells, yeast cells, insect cells, animal cells, and mammalian cells, e.g., murine, rat, simian, or human cells.

An "insert" as used herein, is a heterologous nucleic acid sequence that is ligated into a compatible site into a vector. An insert may comprise one or more nucleic acid sequences that encode a polypeptide or polypeptides. An insert may comprise regulatory regions or other nucleic acid elements.

An "isolated" or "purified" polypeptide or polynucleotide, e.g., an "isolated polypeptide," or an "isolated polynucleotide" is purified to a state beyond that in which it exists in nature. For example, the "isolated" or "purified" polypeptide or polynucleotide, can be substantially free of cellular material or other contaminating proteins from the cell or tissue source from which the protein or polynucleotide is derived, or substantially free from chemical precursors or other chemicals when chemically synthesized. The preparation of antigen binding protein having less than about 50% of non-antigen binding protein (also referred to herein as a "contaminating protein"), or of chemical precursors, is considered to be "substantially free." 40%, 30%, 20%, 10% and more preferably 5% (by dry weight), of non-antigen binding protein, or of chemical precursors is considered to be substantially free.

As used herein, the term "library" refers to a plurality of heterogeneous polypeptides or polynucleotides that encode polypeptides of interest. Sequence differences between library members are responsible for the diversity present in the library.

The term "or" is used herein to mean, and is used interchangeably with, the term "and/or," unless context clearly indicates otherwise.

The term "origin of replication", as used herein, refers to the specific nucleotide sequence at which DNA synthesis is initiated.

As used herein, the terms "polynucleotide" include polymeric forms of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, cRNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also includes both double- and single-stranded molecules. Unless otherwise specified or required, any embodiment of this invention that is a polynucleotide encompasses both the double-stranded form and each of two complementary single-stranded forms known or predicted to make up the double-stranded form. A polynucleotide is composed of a specific sequence of four nucleotide bases: adenine (A), cytosine (C), guanine (G), thymine (T), and uracil (U) for thymine when the polynucleotide is RNA. Thus, the term "polynucleotide sequence" is the alphabetical representation of a polynucleotide molecule.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

The terms "polypeptide", "peptide" and "protein" are used interchangeably herein. The term "rare cutting site" refers to a specific nucleotide sequence of DNA at which a particular restriction enzyme cuts the DNA. Some sites occur frequently in DNA (e.g., every several hundred base pairs, others much less frequently (rare-cutter; e.g., every 10,000 base pairs). Sfi I, as described herein, is a rare cutting enzyme that cuts DNA infrequently due to the recognition site of Sfi I.

The term "recombinant nucleic acid" includes any nucleic acid comprising at least two sequences that are not present together in nature. A recombinant nucleic acid may be generated in vitro, for example by using the methods of molecular biology, or in vivo, for example by insertion of a nucleic acid at a novel chromosomal location by homologous or non-homologous recombination.

The term "single-chain immunoglobulin" or "single-chain antibody" (used interchangeably herein) refers to a protein, which has the ability to specifically bind antigen, having a two-polypeptide chain structure consisting of a heavy and a light chain, said chains being stabilized, for example, by interchain peptide linkers.

"Specific binding" of an antigen binding protein means that the protein exhibits appreciable affinity for a particular antigen or epitope and, generally, does not exhibit significant cross-reactivity. "Appreciable" binding includes binding with an affinity of at least $10^6$, $10^7$, $10^8$, $10^9$ M$^{-1}$, or $10^{10}$ M$^{-1}$. Antigen binding proteins with affinities greater than $10^7$ M$^{-1}$ or $10^8$ M$^{-1}$ typically bind with correspondingly greater specificity. Values intermediate of those set forth herein are also intended to be within the scope of the present invention and antibodies of the invention bind to RAGE (Receptor for Advanced Glycation End products) with a range of affinities, for example, $10^6$ to $10^{10}$ M$^{-1}$, or $10^7$ to $10^{10}$ M$^{-1}$, or $10^8$ to $10^{10}$ M$^{-1}$. An antigen binding protein that "does not exhibit significant cross-reactivity" is one that will not appreciably bind to an entity other than its target (e.g., a different epitope or a different molecule). An antigen specific protein specific for a particular epitope will, for example, not significantly cross-react with remote epitopes on the same protein or peptide. Alternatively, specific binding can be determined according to any art-recognized means for determining such binding. Preferably, specific binding is determined according to Scatchard analysis and/or competitive binding assays.

The term "stem-loop" structure, as used herein refers to a 5' and/or 3' region on DNA with palindromic sequences capable of forming a stem loop structure. The stem loop structure is believed to impede translocation, thus, palindromic sequences slow down the movement of ribosomes during translation and prevent ribosomes from "falling off" the mRNA thereby protecting synthesized mRNA and increasing the number of polysomes in the in vitro translation step. In some embodiments, the ribosome display vector of the present invention is capable of forming a 3' stem loop structure. In some embodiments the ribosome display of the present invention is capable of forming a 5' and a 3' stem loop structure. In addition, the 3' region may contain a poly-A or other polynucleotide stretch for later purification of the mRNA from the in vitro translation. Hybridization with a homopolymeric sequence to the in vitro synthesized mRNA is a standard method that is typically employed by one skilled in the art.

The term "vector" refers to a nucleic acid molecule capable of transporting another nucleic acid to which it has been linked. One type of vector is an episome, i.e., a nucleic acid capable of extra-chromosomal replication. Another type of vector is an integrative vector that is designed to recombine with the genetic material of a host cell. Vectors may be both autonomously replicating and integrative, and the properties of a vector may differ depending on the cellular context (i.e., a vector may be autonomously replicating in one host cell type and purely integrative in another host cell type). Vectors capable of directing the expression of expressible nucleic acids to which they are operatively linked are referred to herein as "expression vectors."

Vectors

As used herein, the term "vector" refers to a polynucleotide molecule capable of carrying and transferring another polynucleotide fragment or sequence to which it has been linked from one location (e.g., a host, a system) to another. The term includes vectors for in vivo or in vitro expression systems. For example, vectors of the invention can be in the form of "plasmids" which refer to circular double stranded DNA loops which are typically maintained episomally but may also be integrated into the host genome. Vectors of the invention can also be in linear forms. In addition, the invention is intended to include other forms of vectors which serve equivalent functions and which become known in the art subsequently hereto.

Vectors of the present invention can be used for the expression of polypeptides. Generally, the vectors of the invention include cis-acting regulatory regions operably linked to the polynucleotide that encodes the polypeptides to be expressed. The regulatory regions may be constitutive or inducible. Appropriate trans-acting factors are supplied by the host by an in vitro translation system, by a complementing vector, or by the vector itself upon introduction into the host.

The vectors of the invention can be derived from, but not limited to, bacterial plasmids, from bacteriophage, from yeast episomes, from yeast chromosomal elements, from mammalian viruses, from mammalian chromosomes, and from combinations thereof, such as those derived from plasmid and bacteriophage genetic elements including, but not limited to, cosmids and phagem ids.

The vectors of the invention can include any elements typically included in an expression or display vector including, but not limited to, origin of replication sequences, one or more promoters, antibiotic resistance genes, leader or signal peptide sequences, various tag sequences, stuffer sequences, restriction sites, ribosome binding sites and translational enhancers, having sequences capable of forming stem loop structures for mRNA stability post-transcription, sequences that encode amino acids lacking a stop codon and sequences that encode a bacterial coat protein.

Thus, the invention also provides nucleotide sequences having sequence identity to the sequences contained in the Sequence Listing. Depending on the particular sequence, the degree of sequence identity is preferably greater than 60% (e.g., 60%, 70%, 80%, 90%, 95%, 97%, 99%, 99.9% or more). These homologous sequences include mutants and variants.

General methods for constructing vectors of the present invention are well known in the art. For example, see *Molecular Cloning: a Laboratory Manual:* 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Current Protocols in Molecular Biology*, Second Edition, Ausubel et al. eds., John Wiley & Sons, 1992. The disclosures of Sambrook et al. and Ausubel et al. are incorporated herein by reference.

The present invention also provides host cells or other organisms that are introduced to or contain the vectors of the invention. For example, the present invention provides bacteria, mammalian cells, yeast and other cellular system containing the vectors of the invention. Suitable mammalian cells include, but are not limited to, Chinese hamster ovary cells (CHO), HeLa cells, HEK cells, COS cells, NSO mouse melanoma cells and those available through public and commercial sources. An exemplary common bacterial host is *E. coli.*

Compatible Restriction Sites

The vectors of the invention include one or more compatible restriction sites between the polynucleotide vector system that facilitate transfer of the polynucleotide sequence encoding the polypeptide of interest (e.g., expressed or displayed polypeptide) between polynucleotide vector system libraries using enzyme digestion and ligation methods well known to those of skill in the art. As used herein, the term "compatible restriction site" refers to a restriction site on one type of vector (e.g., phage display vector) that is compatible with at least one restriction site on a different type of vector (e.g., ribosome display vector). As used herein, restriction sites are "compatible" if, once cleaved by appropriate restriction enzymes, can be ligated by a DNA ligase. In some embodiments, the compatible restriction sites include those double-stranded sequences that, once cleaved by appropriate restriction enzymes, generate "sticky ends" with complementary overhang sequences that can be joined by a DNA ligase. Sticky-end fragments can be ligated not only to the fragment from which it was originally cleaved by a particular restriction enzyme, but also to any other fragment with a compatible sticky end. The sticky end is also called a cohesive end or complementary end. As used herein, compatible restriction sites also include those double-stranded sequences that, once cleaved by appropriate restriction enzymes, generate "blunt ends" that can be joined by a DNA ligase. Blunt ends on a double stranded sequence of DNA have no 5' or 3' overhang and can be ligated to any other blunt ended DNA fragment regardless of the restriction enzyme, as long as the enzyme is a "blunt cutting" enzyme. As used in this application, compatible restriction sites are also referred to as generic restriction sites or universal restriction sites.

In general, any restriction sites cleavable by any type 1, type 2 or type 3 restriction enzymes can be used for the invention. Type I restriction endonucleases cut at a site that differs, and is some distance (at least 1000 bp) away, from their recognition site. The recognition site is asymmetrical and is composed of two portions—one containing 3-4 nucleotides, and another containing 4-5 nucleotides—separated by a spacer of about 6-8 nucleotides. Several enzyme cofactors, including S-Adenosyl methionine (AdoMet), hydrolyzed adenosine triphosphate (ATP) and magnesium ($Mg^{2+}$) ions, are required for their activity. Typical type II restriction enzymes differ from type I restriction enzymes in several ways. They are composed of only one subunit, their recognition sites are usually undivided and palindromic and 4-8 nucleotides in length, they recognize and cleave DNA at the same site, and they do not use ATP or AdoMet for their activity—they usually require only $Mg^{2+}$ as a cofactor. The restriction enzymes and their recognition sequences are well known in the art. Exemplary restriction recognition sites are listed in Table 1. The sequences of suitable restriction sites can be incorporated into a vector sequence using standard recombinant technology.

A vector of the invention includes one or more compatible restriction sites flanking the polynucleotide sequence encoding a polypeptide of interest (e.g., a displayed or expressed polypeptide) so that a nucleic acid fragment containing the entire polypeptide coding sequence can be generated by restriction enzyme digestion. In some embodiments, a vector of the invention contains a first compatible restriction site at the 5' region flanking the encoding sequence of a displayed or expressed polypeptide and a second restriction site at the 3' flanking region of the polypeptide-encoding sequence. In some embodiments, the first and second compatible restriction sites are cleavable by a same restriction enzyme. In some embodiments, the first and second compatible restriction sites are non-compatible with each other. In some embodiments, the 5' compatible site on a first vector is only compatible with the corresponding 5' compatible site on a second vector and the 3' compatible sites on the first vector is only compatible with the corresponding 3' compatible site on the second vector, so that the polypeptide-encoding nucleic acid fragment can be transferred in the correct orientation. In some embodiments, compatible restriction sites suitable for the invention include restriction sites able to be cleaved by restriction enzymes that don't cut or don't cut frequently in the nucleotide sequences encoding displayed or expressed polypeptides. For example, suitable compatible restriction sites can be any sites cleavable by restriction enzymes that cut, on average, less than 30%, 25%, 20%, 15%, 10%, 5%, 4%, 3%, 2%, 1%, 0.08%, 0.06%, 0.04%, 0.02%, 0.01%, or 0.005% of the population of genes encoding the displayed or expressed polypeptides. The cutting frequency of restriction enzymes is dependent upon the nucleotide composition or the DNA source of the coding region. In some embodiment, the vectors of the present invention include one or more restriction sites cleavable by restriction enzymes that don't cut or don't cut frequently in antibody V genes including, but not limited to, Apa LI, Asc I, Ava I, Mfe I, Bst EII, Hind III, Not I, Xba I, Xho I, Xma I, Nco I, Pci I, Pst I, Nhe I, Sac I, Sfi I and Bss H2. In some embodiments, the vectors of the invention may contain restriction sites cleavable by any one of the above enzymes. In some embodiments, the vectors of the invention may contain a combination of restriction sites cleavable by any of the above enzymes, such as but not limited to Asc I and Mfe I; Asc I and Sfi I; Apa LI and Not I; Apa LI and Nhe I; or Apa L 1 and Bst EII. In some embodiments, the vectors of the invention may contain one or more restriction sites cleavable by Sfi I. In some embodiments, the vectors of the invention may contain a first restriction site cleavable by Sfi I and a second restriction site cleavable by Sfi I, wherein the first and second restriction sites are non-compatible with each other. In some embodiments the sequence of the first Sfi I restriction sequence comprises SEQ ID NO. 5. In some embodiments the sequence of the second Sfi I restriction sequence comprises SEQ ID NO. 6 In some embodiments the first and second Sfi I restriction sequences are not compatible with each other. In some embodiments the first and second Sfi I restriction sequences can be interchanged.

Thus, the present invention allows the sequence-independent transfer of encoding polynucleotides between vectors using, for example, a single restriction enzyme digestion that cuts rarely in the polypeptide-encoding polynucleotide sequences. The invention significantly reduces or eliminates the need for PCR steps which are often needed in transfer of gene sequences between vectors and which can lead to mutations of the encoding sequences.

TABLE 1

Exemplary restriction enzymes and corresponding recognition sites In most cases, only the sequences of the up strand are shown (from 5' to 3'). Where the bottom strand is shown, the 3' is on the left.

| ENZYME | RECOGNITION SITE |
|---|---|
| Aat II | GACG▼C |
| AccI | GT▼(A/T)(T/G)AC |
| AccIII | T▼CCGGA |
| Acc65 I | G▼GTACC |
| AccB7 I | CCANNNN▼NTGG (SEQ ID NO. 7) |
| AcyI | G(A/G)▼CG(T/C)C |
| Age I | A▼CCGGT |
| Alu I | AG▼CT |
| A/w26 I | G▼TCTC(1/5) |
| A/w441 | G▼TGCAC |
| Apa I | GGGCC▼C |
| Ava I | C▼(T/C)CG(A/G)G |
| Ava II | G▼G(A/T)CC |
| Ba/I | TGG▼CCA |
| BamH I | G▼GATCC |
| Ban I | G▼G (T/C)(A/G)CC |
| Ban II | G(A/G)GC(T/C)▼C |
| Bbu I | GCATG▼C |
| Bc/I | T▼GATCA |
| Bgl I | GCCNNNN▼NGGC (SEQ ID NO. 8) |
| Bg/II | A▼GATCT |
| BsaM I | GATTGCN▼ |
| BsaO I | CG(A/G)(T/C)▼CG |
| Bsp1286 I | G(G/A/T)GC(C/A/T)▼C |
| BsrBR I | GATNN▼NNATC (SEQ ID NO. 9) |
| BsrS I | ACTGGN▼ |
| BssH II | G▼CGCGC |
| Bst71 I | GCAGC(8/12) |
| Bst98 I | C▼TTAAG |
| Bst E II | G▼GTNACC |
| Bst O I | CC▼(A/T)GG |
| Bst X I | CCANNNNN▼NTGG (SEQ ID NO. 10) |
| Bst Z I | C▼GGCCG |

TABLE 1-continued

Exemplary restriction enzymes and corresponding recognition sites In most cases, only the sequences of the up strand are shown (from 5' to 3'). Where the bottom strand is shown, the 3' is on the left.

| ENZYME | RECOGNITION SITE |
|---|---|
| Bsu36 I | CC▼TNAGG |
| Cfo I | GCG▼C |
| Cla I | AT▼CGAT |
| Csp I | CG▼G(A/T)CCG |
| Csp 45 I | TT▼CGAA |
| Dde I | C▼TNAG |
| Dpn I | G$^{me}$A▼TC |
| Dra I | TTT▼AAA |
| EclHK I | GACNNN▼NNGTC (SEQ ID NO. 11) |
| Eco47 III | ACG▼GCT |
| Eco52 I | C▼GGCCG |
| Eco72 I | CAC▼GTG |
| Ecol CR I | GAG▼CJC |
| EcoR I | G▼AATTC |
| EcoR V | GAT▼ATC |
| Fok I | GGATG(9/13) |
| Hae II | (A/G)GCGC▼(T/C) |
| HaeIII | GG▼CC |
| Hha I | GCG▼C |
| Hinc II | GT(T/C)▼(A/G)AC |
| Hind III | A▼AGCTT |
| Hinf I | G▼ANTC |
| Hpa I | GTT▼AAC |
| Hpa II | C▼CGG |
| Hsp92 I | G(A/G)▼CG(T/C)C |
| Hsp92 II | CATG▼ |
| I-Ppo I | CTCTCTTAA▼GGTAGC (SEQ ID NO. 12) |
| Kpn I | GGTAC▼C |
| Mbo I | ▼GATC |
| Mbo II | GAAGA(8/7) |
| Mlu I | A▼CGCGT |
| Msp I | C▼CGG |
| MspA I | C(A/C)G▼C(G/T)G |
| Nae I | GCC▼GGC |
| Nar | GG▼CGCC |
| Nci I | CC▼(G/C)GG |
| Nco I | C▼CATGG |
| Nde I | CA▼TATG |
| NgoM I | G▼CCGGC |
| Nhe I | G▼CTAGC |
| Not I | GC▼GGCCGC |
| Nru I | TCG▼CGA |
| Nsi I | ATGCA▼T |
| Pst I | CTGCA▼G |
| Pvu I | CGAT▼CG |
| Rvu II | CAG▼CTG |
| Rsa I | GT▼AC |
| Sac I | GAGGCT▼C |
| Sac II | CCGC▼GG |
| Sal I | G▼TCGAC |
| Sau3A I | ▼GATC |
| Sau96 I | G▼GNCC |
| Sca I | AGT▼ACT |
| Sfi I | GGCCNNNN▼NGGCC (SEQ ID NO. 13) |
| Sgf I | GCGAT▼CGC |
| Sin I | G▼G(A/T)CC |
| Sma I | CCC▼GGG |
| SnaB I | TAC▼GTA |
| Spe I | A▼CTAGT |
| Sph I | GCATG▼C |
| Ssp I | AAT▼ATT |
| Stu I | AGG▼CCT |
| Sty I | C▼C(A/T)(T/A)GG |
| Taq I | T▼CGA |
| Tru9 I | T▼TAA |
| TthIII I | GACN▼NNGTC |

TABLE 1-continued

Exemplary restriction enzymes and corresponding recognition sites In most cases, only the sequences of the up strand are shown (from 5' to 3'). Where the bottom strand is shown, the 3' is on the left.

| ENZYME | RECOGNITION SITE |
|---|---|
| Vsp I | A▼TAAT |
| Xba I | T▼CTAGA |
| Xho I | C▼TCGAG |
| Xho II | (A/G)▼GATC(T/C) |
| Xma I | C▼CCGGG |
| Xmn I | GAANN▼NNTTC (SEQ ID NO. 14) |

Phage Display Vectors

A phage display vector of the present invention is a vector containing phage derived polynucleotide sequences capable of expressing, or conditionally expressing, a heterologous polypeptide, for example, as a fusion protein with a phage protein (e.g., a phage surface protein). In some embodiments, a phage display vector of the present invention is a vector derived from a filamentous phage (e.g., phage f1, fd, and M13) or a bacteriophage (e.g., T7 bacteriophage and lambdoid phages. The filamentous phage and bacteriophage are described in e.g., Santini (1998) *J. Mol. Biol.* 282:125-135; Rosenberg et al. (1996) *Innovations* 6:1-6; Houshmand et al. (1999) *Anal Biochem* 268:363-370).

In general, a phage display vector of the invention can include the following elements: (1) a promoter suited for constitutive or inducible expression (e.g., lac promoter); (2) a ribosome binding site and signal sequence preceding the sequence encoding a displayed peptide; and (3) one or more compatible restriction sites, in particular, restriction sites compatible to a ribosome display vector of the present invention as described below; (4) optionally, a tag sequence such as a stretch of 5-6 histidines or an epitope recognized by an antibody; (5) a second tag sequence (6)a suppressible codon (e.g., a termination codon); and (7) a sequence encoding a phage surface protein positioned in-frame to form a fusion to the peptide to be displayed. In general, a phage display vector of the invention contains a promoter and/or regulatory region operably linked to a polynucleotide sequence encoding the heterologous polypeptide of interest and a sequence encoding a phage surface protein. The term "operably linked" refers to a functional linkage between nucleic acid sequences such that the linked promoter and/or regulatory region functionally controls expression of the coding sequence. It also refers to the linkage between coding sequences such that they may be controlled by the same promoter and/or regulatory region. Such linkage between coding sequences may also be referred to as being linked in frame or in the same coding frame such that a fusion protein comprising the amino acids encoded by the coding sequences may be expressed.

In other embodiments of the invention, the ability of the phage display vector to express a fusion protein is regulated in part by use of a regulated promoter or other regulatory region (e.g., an inducible promoter such that in the absence of induction, expression controlled by them is low or undetectable). Non-limiting examples of inducible promoters include the lac promoter, the lac UV5 promoter, the arabinose promoter, and the tet promoter. In some embodiments, an inducible promoter can be further restricted by incorporating repressors (e.g., lacI) or terminators (e.g., a tHP terminator). For example, repressor lac! and be used together with the Lac promoter. In some embodiments, a strong tHP terminator can be additionally inserted between the lacI gene and the Lac promoter. As used herein, the term "phage surface protein" refers to any protein normally found at the surface of a filamentous phage (e.g., phage f1, fd, and M13) or a bacteriophage (e.g., λ, T4 and T7) that can be adapted to be expressed as a fusion protein with a heterologous polypeptide and still be assembled into a phage particle such that the polypeptide is displayed on the surface of the phage. Suitable surface proteins derived from filamentous phages include, but are not limited to, minor coat proteins from filamentous phages, such as gene III proteins, and gene VIII proteins, major coat proteins from filamentous phages, such as, gene VI proteins, gene VII proteins, gene IX proteins, gene 10 proteins from T7, and capsid D protein (gpD) of bacteriophage λ. In some embodiments, a suitable phage surface protein is a domain, a truncated version, a fragment, or a functional variant of a naturally occurring surface protein. For example, a suitable phage surface protein can be a domain of the gene III protein, e.g., the anchor domain or "stump." Additional exemplary phage surface proteins are described WO 00/71694, the disclosures of which are hereby incorporated by reference. As appreciated by the skilled artisan, the choice of a phage surface protein is to be made in combination with a consideration of the phage display vector and the cell to be used for propagation thereof.

The displayed polypeptide is typically covalently linked to the phage surface protein. The linkage results form translation of a nucleic acid encoding the polypeptide component fused to the surface protein. The linkage can include a flexible peptide linker, a protease site, or an amino acid incorporated as a result of suppression of a stop codon.

Suppressible codons are known in the art. For example, suppressible codons can be termination codons including UAG (referred to as the amber codon), UAA (referred to as the ochre codon), and UGA. UAG, UAA and UGA indicate the mRNA codon. The choice of termination codon can also be augmented by introduction of particular sequences around the codon.

A specific initiation signal may be incorporated to further regulate translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. A low efficiency ribosome-binding sequence or translation initiation signal may be used to further decrease protein production without induction.

Any peptide sequences capable of driving or directing secretion of expressed protein or polypeptide can be used as leader sequences for the phage display vectors. Exemplary leader sequences include, but not limited to, a PelB leader sequence and an Omp A leader sequence.

In addition, optionally, a fusion polypeptide can include a tag that may be useful in purification, detection and/or screening. Suitable tags include, but not limited to, a FLAG tag, poly-histidine tag, a gD tag, a c-myc tag, green fluorescence protein tag, a GST tag or β-galactosidase tag.

Restriction sites can be incorporated in the 5' and 3' untranslated regions to flank a coding sequence for a displayed peptide of interest. For example, a first compatible restriction site can be incorporated in the C-terminus of the leader sequence and the second compatible site can be incorporated upstream or within the tag sequences. A stuffer sequence can be included between the first and second compatible restriction sites. The stuffer sequence can be cleaved and replaced with the coding sequence for displayed polypeptide using the compatible restriction sites. Typically, a stuffer sequence is designed to make the double-cut plasmid easily distinguishable from single-cut plasmid during agarose gel purification. In some embodiments, the stuffer sequence can include an antibiotic resistance gene to allow double antibiotic selection of bacteria after transformation with plasmid that does not yet contain a cloned polypeptide encoding sequence. In some embodiments, the stuffer sequence between the two non-compatible restriction sites comprises a nucleotide sequence that codes for an antibiotic resistance gene under a separate promoter than that which drives expression of a coding sequence of an antigen binding polypeptide of interest.

General methods for constructing phage display vectors, phage display libraries and the method of use are described, for example, in Ladner et al., U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al. (1998) *Immunotechnology* 4:1-20; Hoogenboom et al. (2000) *Immunol. Today* 2:371-8; Fuchs et al. (1991) *Bio/Technology* 9:1370-1372; Hay et al. (1992) *Hum Antibod Hybridomas* 3:81-85; Huse et al. (1989) *Science* 246:1275-1281; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrard et al. (1991) *Bio/Technoloqy* 9:1373-1377; Rebar et al. (1996) *Methods Enzymol.* 267:129-49; Hoogenboom et al. (1991) *Nuc Acid Res* 19:4133-4137; and Barbas et al. (1991) *PNAS* 88:7978-7982.

Exemplary phage display vectors of the invention are described in the example section.

Ribosome Display Vectors

The ribosome display vectors of the present invention include vectors suitable for prokaryotic or eukaryotic display system. A prokaryotic ribosome display system is also referred to as polysome display system.

A ribosome display vector of the invention typically includes a promoter or RNA polymerase binding sequence, a ribosome binding site, a translation initiation sequence, a nucleic acid encoding an amino acid spacer sequence separating the expressed displayed peptide of interest from the ribosome after translation to assist correct folding of the peptide.

Optionally, the ribosome display vector may also include one or more sequences encoding detection tags, 3' stem loop structure and/or 5' stem loop structure to protect synthesized mRNA, a translation enhancer or "activator" sequence(s). Typically, the ribosome display vector of the invention lacks a stop codon in-frame of the displayed polypeptide.

The promoter or RNA polymerase binding sequence suitable for the invention may include any promoters suitable for in vitro translation. Exemplary promoters include, but are not limited to, T7, T3, or SP6 promoters, or any sequences recognized by RNA polymerases T7, T3 or SP6. In some embodiments, a ribosome display vector of the invention may include two promoters, such as both the T7 and SP6 promoters. A ribosomal binding site may be positioned upstream, downstream or within the promoter region. This ribosome binding site may be specific for prokaryotic ribosomal complexes, for example a Shine-Dalgarno sequence, if a prokaryotic translation procedure is used.

Suitable prokaryotic translation systems include, but are not limited to E. coli S30 system. The ribosome binding site may also be specific for a eukaryotic translation system, for example a Kozak consensus sequence, if a eukaryotic translation procedure is used. A suitable eukaryotic translation system includes, but is not limited to, the rabbit reticulocyte system (Krawetz et al., *Can. J. Biochem. Cell. Biol.* 61:274-286, 1983; Merrick, *Meth. Enzvmol.* 101:38, 1983). One exemplary Kozak consensus sequence is GCCGCCAC-CATGG (SEQ ID NO. 15). Additional translation enhancer sequences may also be included. For example, the translation enhancer of *X. leavis* β globin gene may be inserted between the promoter and translation initiation site. Other exemplary translation enhancers or activator sequences include, but are limited to, untranslated "leader sequences" from tobacco mosaic virus (Jobling et al. *Nucleic Acids Res.* 16:4483-4498, 1988), 5' untranslated region from alfalfa mosaic virus RNA 4 (Jobling and Gehrke, *Nature* 325:622-625, 1987), black beetle virus (Nodavirus) RNA 2 (Friesen and Rueckert, *J. Virol.* 37:876-886, 1981), and turnip mosaic virus, and brome mosaic virus coat protein mRNAs (Zagorski et al., *Biochimie* 65:127-133, 1983).

An amino acid spacer sequence can be engineered into the nucleic acid that will be fused or linked at the C-terminus of the displayed peptide to separate it from the ribosome upon translated. It is contemplated that the spacer sequence allows the displayed polypeptide to exit completely from the ribosome "tunnel" and to fold correctly, yet leave the translated polypeptide on the ribosome due to the lack of a stop codon which essentially freezes the peptide onto the ribosome, yet still attached to the RNA from which the polypeptide is translated from. Typically, a suitable spacer sequence encodes at least 20 amino acids in length. In particular, a suitable spacer length may include at least 30 amino acids, 40 amino acids, 50 amino acids, 60 amino acids, 70 amino acids, 80 amino acids, 90 amino acids, 100 amino acids. In certain embodiments, the spacer includes 23 amino acids. In certain embodiments, the spacer includes 69 amino acids. In certain embodiments, the spacer includes 116 amino acids. Suitable spacer sequences can be derived from any known proteins, such as but not limited to the constant region of immunoglobulin kappa chain (C1c), gene III of filamentous phage M13, and the CH3 domain of human IgM. A tag sequence may be incorporated into the ribosome display vector of the invention. Typically, the tag sequence is incorporated at the N terminus or C terminus of the displayed polypeptide. In some embodiments, the tag sequence is at the N-terminal of the translated polypeptide. Suitable tags include, but are not limited to, a stretch of histidines (e.g., 5-6 histidines), an epitope recognized by an antibody for example: substance P, a flag tag or c-myc tag.

The ribosome display vector may also include a 5' and/or 3' region with palindromic sequences capable of forming a stem loop structure. The stem loop structure is believed to impede translocation, thus, palindromic sequences slow down the movement of ribosomes during translation and prevent ribosomes from "falling off" the mRNA thereby protecting synthesized mRNA and increasing the number of polysomes in the in vitro translation step. In some embodiments, the ribosome display vector of the present invention is capable of forming a 3' stem loop structure. In some embodiments the ribosome display of the present invention is capable of forming a 5' and a 3' stem loop structure. In addition, the 3' region may contain a poly-A or other polynucleotide stretch for later purification of the mRNA from the in vitro translation. Hybridization with a homopolymeric sequence to the in vitro synthesized mRNA is a standard method that is typically employed by one skilled in the art.

To facilitate transfer of the entire nucleic acid fragment encoding the polypeptide of interest, the ribosome display vector of the present invention as described above, typically includes restriction sites compatible with the phage display of the present invention, as described above, flanking the polypeptide-encoding sequence. In some embodiments, the ribosome display vector includes a first restriction site 5' of the coding region of the polypeptide of interest in the untranslated region and a second restriction site 3' downstream to the polypeptide-encoding sequence. In some embodiments, the first and second restriction sites of the ribosome display vector are not compatible with each other. In some embodiments, the phage display vector of the invention includes a first restriction site located 5' to the coding region of the polypeptide of interest in the untranslated region and a second restriction site located 3' downstream to the polypeptide encoding sequence, but the first and second restriction sites of the phage display vector are not compatible with each other. In some embodiments, the first restriction site of the ribosome display vector and the first restriction site of the phage display vector are compatible and can be ligated together, while the second restriction site of the ribosome display vector and the second restriction site of the phage display vector are compatible and can be ligated together. The compatibility of the compatible restriction sites within each vector of the present invention facilitates transfer of the entire population of polynucleotides that encode for the polypeptide(s) of interest from one vector to the other.

The ribosome display vector may be chemically synthesized by protocols well known to those skilled in the art. Alternatively, each of the above elements may be incorporated into one or more plasmids, amplified in microorganisms, purified by standard procedures, and cut into appropriate fragments with restriction enzymes before assembly into the vector. General methods for constructing ribosome display vectors, ribosome display libraries and method of use are described in U.S. Pat. Nos. 5,643,768, 5,658,754, and 7,074,557, and in Mattheakis et al., (1994) *PNAS USA* 91, 9022 9026; Mattheakis et al., (1996) *Methods Enzymol.* 267, 195 207; Gersuk et al., (1997) *Biotech and Biophys. Res. Corn.* 232, 578 582; Hanes and Pluckthun (1997) *PNAS USA* 94, 4937 4942; Hanes et al., (1998) *PNAS USA* 95, 14130 50; He and Taussig (1997) *NAR* 5132 5234, the teachings of all of which are hereby incorporated by reference.

Exemplary ribosome display vectors of the present invention are described in the Examples section.

Displayed Peptides

As used herein, the term "displayed polypeptide," "displayed peptide," "displayed protein," or grammatical equivalents thereof refer to a heterologous polypeptide encoded by a nucleic acid sequence not part of the vector sequence (ie, a heterologous nucleic acid sequence encoding a polypeptide that has been ligated into the vector sequence). As used herein, the term "antigen binding polypeptide" can be used interchangeably with the terms "displayed polypeptides" etc., as described above. Typically, displayed polypeptides are those encoded by nucleic acid sequences derived from eukaryotic or prokaryotic cells, especially, but not limited to, those from human beings, plants, plant cells, bacteria, fruit flies, yeast, zebrafish, and non-human mammals including, but not limited to, mice, rats, rabbits, non-human primates, cattle, sheep, horses, dogs and cats. In some embodiments, the displayed antigen binding polypeptides include clinically relevant gene products including potential targets for the identification of drugs for particular disease indications. In particular, the displayed polypeptides include polypeptides from an antigen binding family. The antigen binding family refers to a population of polypeptides which retain characteristics of molecules that specifically bind to antigens of interest. The members of this family of polypeptides can be involved in many aspects of cellular and non-cellular interactions in vivo, including widespread roles in the immune system (for example, antigen binding polypeptides which may include antibodies and fragments thereof as well as non-antibody antigen binding polypeptide, T-cell receptor molecules and the like, molecules involvement in cell adhesion and molecules involved in intracellular signaling. The present invention is applicable to all antigen binding polypeptide molecules which may include: a peptide, a chimeric antibody, a humanized antibody, a human antibody, a single chain antibody, a tetrameric antibody, a tetravalent antibody, a multispecific antibody, a domain-specific antibody, a domain-deleted antibody, a fusion protein, an ScFc fusion protein, an Fab fragment, an Fab' fragment, an F(ab')2 fragment, an Fv fragment, a single-chain Fv (ScFv) fragment, an Fd fragment, a single domain antibody, a dAb fragment, a small modular immunopharmaceutical (SMIP), a shark variable IgNAR domain, as described in WO 03/014161, a CDR3 peptide, a constrained FR3-CDR3-FR4 peptide, a nanobody as described in US 20080107601, a bivalent nanobody and a minibody.

Collection

As used herein, the term "collection" is a population of diverse variants, for example, nucleic acid variants which differ in nucleotide sequence or polypeptide variants which differ in amino acid sequence.

Library

As used herein, the term "library" refers to a plurality of heterogeneous polypeptides or polynucleotides that encode polypeptides of interest. Sequence differences between library members are responsible for the diversity present in the library. The library may take the form of a mixture of polypeptides or polynucleotides, or may be in the form of organisms or cells, for example bacteria, viruses, animal or plant cells and the like, transformed with a library of nucleic acids. As used herein, the term "organism" refers to all cellular life-forms, such as prokaryotes and eukaryotes, as well as non-cellular, nucleic acid-containing entities, such as bacteriophage and viruses.

In particular, antibody libraries can incorporate diversity from a variety of sources, including but not limited to synthetic nucleic acid, naive nucleic acids, nucleic acid from subjects (e.g., immunized or diseased human subjects), and animals (e.g., immunized animals).

In some embodiments, immune cells encompassing antigen binding polypeptides from the group consisting of: a peptide, a chimeric antibody, a humanized antibody, a human antibody, a single chain antibody, a tetrameric antibody, a tetravalent antibody, a multispecific antibody, a domain-specific antibody, a domain-deleted antibody, a fusion protein, an ScFc fusion protein, an Fab fragment, an Fab' fragment, an F(ab')2 fragment, an Fv fragment, a single-chain Fv (ScFv) fragment, an Fd fragment, a single domain antibody, a dAb fragment, a small modular immunopharmaceutical (SMIP), a shark variable IgNAR domain, a CDR3 peptide, a constrained FR3-CDR3-FR4 peptide, a nanobody, a bivalent nanobody and a minibody. as well as polypeptides from MHC-complexes and T cell receptors. The antigen binding polypeptides may be derived from immune cells and can be obtained from but not limited to a human, a primate, mouse, rabbit, camel, or rodent. The cells can be selected for a particular property. For example, T cells that are CD4+ and CD8– can be selected. B cells at various stages of maturity can be selected. Immune cells can be used as a natural source of diversity regarding the expression of different varieties of genes that can then be converted to cDNA and cloned into the polynucleotides of the present invention.

Naturally diverse sequences can be obtained as cDNA produced from total RNAs isolated from cells and samples obtained from a subject, as described herein. RNA isolated from said sources listed are reverse transcribed in any manner with any suitable primer by procedures well known by those of ordinary skill in the art. The primer binding region can be constant among different antigen binding proteins e.g., in order to reverse transcribe different isotypes of polypeptides of interest. The primer binding region can also be specific to a particular isotype of polypeptide as well. cDNA can be amplified, modified, fragmented, or ligated into a polypeptide to form an antigen binding polypeptide encoding library. See, e.g., de Haard et al. (1999) supra.

In some embodiments, the library of the invention comprises an ScFv library and can be constructed according to the method known in the art. See, e.g., Griffiths et al., 1994; Vaughan et al., 1996; Sheets et al., 1998; Pini et al., 1998; de Haard et al., 1999; Knappik et al., 2000; Sblattero and Bradbury, 2000). One or more restriction sites can be incorporated into the cDNA, as synthesized as described above, by proper primer design using methods well known in the art.

For example, a method of constructing a phage display library may include the steps of: (1) digesting a plurality of phage display vectors of the invention with one or more restriction enzymes that cleave one or more restriction sites; and (2) ligating a population of fragments, each of which contains a nucleic acid sequence encoding a peptide to be displayed, into the plurality of phage display vectors from step (1) using the one or more restriction sites. In some embodiments, the restriction enzyme is Sfi I and the compatible restriction sites include one or more Sfi I sites, in particular, non-compatible Sfi I sites.

As another example, a method for constructing a ribosome display library may include the steps of: (1) digesting a plurality of ribosome display vectors of the invention with one or more restriction enzymes that cleave one or more compatible restriction sites; and (2) cloning a population of fragments, each of which contains a nucleic acid sequence encoding a peptide to be displayed, into the plurality of ribosome display vectors from step (1) using the one or more compatible restriction sites. In some embodiments, the restriction enzyme is Sfi I and the compatible restriction sites include one or more Sfi I sites, in particular, non-compatible Sfi I sites.

Conversion Between Libraries

The library design strategy of the present invention allows the sequence-independent transfer of polypeptide-encoding sequences between vectors using restriction enzyme-based strategy. In particular, using compatible restriction sites present at fixed positions in all selected protein libraries facilitates the movement of large pools of protein variants using a one-step cloning procedure. In some embodiments, the one-step cloning procedure involves a single restriction enzyme (e.g., Sfi I) digestion.

In some embodiments, a method of generating a ribosome display library from a phage display library that encodes an antigen binding polypeptide comprises the following steps:

a) identifying the polynucleotide(s) that encode(s) a polypeptide that has been shown to bind to an antigen of interest in a phage display assay, b) the polynucleotide is isolated, c) whereby a plurality of the polynucleotides that encode said polypeptide is generated by digesting the polynucleotides with a restriction enzyme. In some embodiments the restriction enzyme is Sfi I, d) a ribosome display vector of the present invention is prepared by digesting with a restriction enzyme. In some embodiments, the restriction enzyme is Sfi I. The polynucleotides of b) are ligated to the polynucleotide in d).

In some embodiments, a method for transferring a nucleic acid fragment encoding a displayed peptide from a ribosome display vector to a phage display vector includes the steps of: (1) providing a ribosome display vector containing a fragment encoding a displayed peptide; (2) retrieving the fragment encoding the displayed peptide by digesting the ribosome display vector using one or more restriction enzymes; (3) providing a phage display vector containing one or more restriction sites compatible with the recognition sites of the one or more restriction enzymes used in step (2); and (4) cloning the fragment from step (2) into the phage display vector using the one or more compatible restriction sites.

In other embodiments, a method for transferring a population of nucleic acid fragments encoding displayed peptides from a ribosome display library to a phage display library includes the steps of: (1) providing a ribosome display library including a plurality of vectors including a population of nucleic acid fragments, each of the population of nucleic acid fragments encodes a displayed peptide; (2) retrieving the population of nucleic acid fragments by digesting the ribosome display library with one or more restriction enzymes; (3) providing a plurality of phage display vectors, each containing one or more restriction sites compatible with the recognition sites of the one or more restriction enzymes used in step (2); and (4) cloning the population of nucleic acid fragments into the plurality of phage display vectors using the one or more compatible restriction sites.

Methods of Identification of Antigen Binding Protein

Some exemplary selection processes for the determination and identification of antigen binding proteins are as follows.

Panning. A target molecule is immobilized to a solid support such as a surface of a microtitre well, matrix, particle, or bead. The display library is contacted to the support. Library members that have affinity for the target are allowed to bind. Non-specifically or weakly bound members are washed from the support. Then the bound library members are recovered (e.g., by elution) from the support. Recovered library members are collected for further analysis (e.g., screening) or pooled for an additional round of selection.

Magnetic Particle Processor. One example of an automated selection uses magnetic particles and a magnetic particle processor. In this case, the target is immobilized on the magnetic particles. The KingFisher™ system, a magnetic particle processor from Thermo LabSystems (Helsinki, Finland), is used to select display library members against the target. The display library is contacted to the magnetic particles in a tube. The beads and library are mixed. Then a magnetic pin, covered by a disposable sheath, retrieves the magnetic particles and transfers them to another tube that includes a wash solution. The particles are mixed with the wash solution. In this manner, the magnetic particle processor can be used to serially transfer the magnetic particles to multiple tubes to wash non-specifically or weakly bound library members from the particles. After washing, the particles are transferred to a tube that includes an elution buffer to remove specifically and/or strongly bound library members from the particles. These eluted library members are then individually isolated for analysis or pooled for an additional round of selection. Detailed magnetic particle processor selection processes are described in U.S. Application Publication No. 20030224408.

Cell-Based Selections. The selection can be performed by binding the display library to target cells, and then selecting for library members that are bound by the cells. Cell-based selections enable the identification of ligands that recognize target molecules as presented in their natural milieu, e.g., including post-translational modifications, associated proteins and factors, and competing factors. Further, since cell-based selections are not directed against a specific singular target molecule, no a priori information is required about the target. Rather, the cell itself is a determinant. Later steps, particular functional assays, can be used to verify that identified ligands are active in targeting effector functions to the cell. Detailed cell-based selection processes are described in U.S. Application Publication No. 20030224408.

In vivo Selections. The selection can be done in vivo to identify library members that bind to a target tissue or organ, e.g., as described in Kolonin et al. (2001) *Current Opinion in Chemical Biology* 5:308-313, Pasqualini and Ruoslahti (1996) *Nature* 380:364-366, and Paqualini et al. (2000) "In vivo Selection of Phage-Display Libraries" *In Phage Display: A Laboratory Manual Ed.* Barbas et al. Cold Spring Harbor Press 22.1-22.24. For example, a phage display library is injected into a subject (e.g., a human or other mammal). After an appropriate interval, a target tissue or organ is removed from the subject and the display library members that bind to the target site are recovered and characterized.

Affinity Maturation/Optimization of Antigen Binding Protein

In some embodiments, after initial selection using a first library, a selected population of library members can be mutagenized to improve the binding affinity or any other properties of the selected members. For example, a first display library is used to identify one or more ligands for a target (also known as lead identification). These identified ligands are then mutated to form a second display library. Additional diversity is introduced by mutagenesis. Higher affinity ligands are then selected from the second library, e.g., by using higher stringency or more competitive binding and washing conditions. This process is known as affinity maturation or optimization.

In some embodiments, a phage display library of the present invention is used for initial identification of target-binding polypeptides. The selected pool of nucleic acid fragments encoding the target-binding polypeptides can be retrieved by digestion using restriction enzymes that cleave one or more compatible restriction sites. The retrieved fragments can then be cloned "en masse" into ribosome display vectors of the present invention using one or more compatible restriction sites. The ribosome display vectors containing the selected nucleic acid fragments transferred from the phage display library can be further mutagenized to form a second library, e.g., a ribosome display library. The diversity of a ribosome display library can be up to more than $10^{12}$.

Numerous techniques can be used to mutate the identified initial ligands to introduce further diversity. These techniques include, but are not limited to, error-prone PCR (Leung et al. (1989) *Technique* 1:11-15), recombination, DNA shuffling using random cleavage (Stemmer (1994) *Nature* 389-391), RACHITT™ (Coco et al. (2001) *Nature Biotech.* 19:354), site-directed mutagenesis (Zoller et al. (1987) *Methods Enzymol.* 1987;154:329-50.; Zoller et al. (1982) *Nucl. Acids Res.* 10:6487-6504), cassette mutagenesis (Reidhaar-Olson (1991) *Methods Enzymol.* 208:564-586) and incorporation of degenerate oligonucleotides (Griffiths et al. (1994) *EMBO J* 13:3245).

For antigen binding proteins, mutagenesis can be directed to the CDR regions of the heavy or light chains. In some embodiments, mutagenesis can be directed to framework regions near or adjacent to the CDRs.

Methods for identification of the members of the ribosome display library with desirable binding affinity or other properties and retrieving the nucleic acid sequences encoding the selected polypeptides are well known in the art. For example, exemplary methods are described in U.S. Pat. Nos. 5,643,768, 5,658,754, and 7,074,557.

Reformatting

Following selection and identification of a library member containing a nucleic acid sequence encoding a displayed polypeptide with desirable properties, the nucleic acid can be retrieved from the display vector and transferred to an expression vector for production or further analysis. This process is typically known as reformatting. Thus, the reformatting process is used, for example, to transfer nucleic acid from a display vector to a vector suitable for bacteria or mammalian cell production. In one embodiment, each selected library member is reformatted individually. In another embodiment, the library members are combined and reformatted en masse.

The reformatting process can be tailored to the expression system used initially for display and for the secondary expression system. For example, the reformatting process is particularly important for the analysis of ribosome display products because typical ribosome vectors are not compatible with bacterial or mammalian expression system, while the same phage display vector can be used to express the selected displayed polypeptide in a bacteria expression system.

Thus, in some embodiments, the nucleic acid sequence encoding a selected displayed polypeptide may be transferred from a ribosome display construct to a phage display vector of the present invention using the compatible restriction sites. In some embodiments, the nucleic acids encoding the selected displayed polypeptides may be transferred en masse from ribosome display constructs to the phage display vectors of the present invention using compatible restriction sites.

In some embodiments, the nucleic acid sequence encoding a selected displayed polypeptide may be transferred from a ribosome display or a phage display construct to a mammalian expression vector, for example, using compatible restriction sites between the vectors of the invention.

In some embodiments, the selected ScFv polypeptide can be reformatted into other immunoglobulin formats including, but not limited to, IgG, ScFv-Fc fusions, F(ab)2, Fab', Fab, diabodies, triabodies, tetrabodies, a chimeric antibody, a humanized antibody, a human antibody, a single chain antibody, a tetrameric antibody, a tetravalent antibody, a multispecific antibody, a domain-specific antibody, a domain-deleted antibody, a fusion protein, an ScFc fusion protein, an F(ab')2 fragment, an Fv fragment, an Fd fragment, a single domain antibody, a dAb fragment, a nanobody, a shark variable IgNAR domain, a CDR3 peptide, and a constrained FR3-CDR3-FR4 peptide. In one example of en masse reformatting, the reformatting of ScFv involves a two-step process. The first cycle includes digesting display vectors to release nucleic acid fragments that include minimally a light chain variable coding region and a heavy chain variable coding region using for example, compatible restriction sites. The fragments are cloned into a vector for mammalian expression. During this step, the transfer of the nucleic acid fragments encoding both VH and VL genes insures that combinations of heavy and light chain present in the display vector are maintained in the expression vector.

Further, the transfer process can be used to switch from a prokaryotic promoter to a mammalian promoter on the 5' end of the coding strand and from a sequence encoding a bacteriophage coat protein (or fragment thereof) to a sequence encoding an Fc domain on the 3' end of the coding strand. General methods for cloning are described in standard laboratory manuals, e.g., Sambrook et al. (2001) *Molecular Cloning: A Laboratory Manual* (Third Edition), Cold Spring Harbor Laboratory Press.

In the second step, the region intervening between the light chain coding region and the heavy chain-coding region is substituted. For example, the linker region between VH and VL genes can be replaced with a sequence that includes a prokaryotic ribosome binding site (RBS), or a sequence with an internal ribosomal entry site (IRES) or a sequence including a eukaryotic promoter. Also in this process, signals for secretion (e.g., the prokaryotic or eukaryotic signals for secretion) and sequences from the constant regions of the immunoglobulin molecules (e.g., Ck, CH1) can be inserted. In some implementations, the intervening region is substituted by recombination in a cell. In still others, the intervening region is not substituted, but rather sequences are inserted e.g., using site-specific recombination, and optionally without excising the sequences designed for prokaryotic expression.

Hybrid signal sequences that are functional in both prokaryotic and eukaryotic cells can be used to obviate reformatting of some (e.g., at least the 3' region of the signal sequence, e.g., the −3, −2, and −1 positions) or all of the signal sequence. In some cases, a signal sequence is functional in multiple expression systems (e.g., both pro- and eukaryotic systems). For example, the signal sequence of some bacterial beta-lactamases is functional in eukaryotic cells and prokaryotic cells. See, e.g., Kronenberg et al., 1983, *J. Cell Biol.* 96, 1117-9; Al-Qahtani et al., 1998, *Biochem. J.* 331, 521-529. Signal sequences that function in multiple hosts can also be designed on the basis of the requirement of such signal sequence (consensus rules) in the respective expression hosts, or may be selected empirically.

In some embodiments, the selected ScFv polypeptide of the invention can be reformatted to small modular immunopharmaceutical (SMIP™) drug format (Trubion Pharmaceuticals, Seattle, Wash.) using a similar cloning strategy. SMIPs are single-chain polypeptides composed of a binding domain for a cognate structure such as an antigen, a counter receptor or the like, a hinge-region polypeptide having either one or no cysteine residues, and immunoglobulin CH2 and CH3 domains (see also www.trubion.com). The SMIP drug designs are disclosed in, e.g., U.S. Published Patent Appln. Nos. 2003/0118592, 2003/0133939, 2004/0058445, 2005/0136049, 2005/0175614, 2005/0180970, 2005/0186216, 2005/0202012, 2005/0202023, 2005/0202028, 2005/0202534, and 2005/0238646, and related patent family members thereof, all of which are hereby incorporated by reference herein in their entireties.

Encoding nucleic acid, whether reformatted or not, may be used in production of the encoded polypeptide or peptide using any technique available in the art for recombinant expression.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli.

The expression of antigen binding proteins, antibodies and antibody fragments thereof in prokaryotic cells such as E. coli is well established in the art. For a review, see for example Pluckthun, A. Bio/Technology 9: 545 551 (1991). Expression in eukaryotic cells in culture is also available to those skilled in the art as an option for production of a specific binding member, see for recent reviews, for example Ref, M. E. (1993) Curr. Opinion Biotech. 4: 573 576; Trill J. J. et al. (1995) Curr. Opinion Biotech. 6: 553 560.

Thus, nucleic acid encoding a specific polypeptide selected using a method of the invention, or a component of such a specific polypeptide (e.g. VH and/or VL domain) may be provided in an expression system for production. This may comprise introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g. by culturing host cells under conditions for production of the encoded product. The present invention also provides a method that comprises using a construct as stated above in an expression system in order to express a specific binding member or polypeptide as above.

Following production by expression, a product may be isolated and/or purified and may be formulated into a composition comprising at least one additional component. Such a composition may comprise a pharmaceutically acceptable excipient, vehicle or carrier. Further aspects and embodiments of the present invention will be apparent to those skilled in the art in the light of the present disclosure. It should further be noted that all documents mentioned anywhere herein are incorporated by reference.

Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise. In addition, the invention encompasses compositions made according to any of the methods for preparing compositions disclosed herein.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, values that are expressed as ranges can assume any specific value within the stated ranges in different embodiments of the invention, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range. In addition, it is to be understood that any particular embodiment of the present invention may be explicitly excluded from any one or more of the claims. Any embodiment, element, feature, application, or aspect of the compositions and/or methods of the invention can be excluded from any one or more claims. For purposes of brevity, all of the embodiments in which one or more elements, features, purposes, or aspects are excluded are not set forth explicitly herein.

EXAMPLES

Example 1.

Design of Phage Display Vectors Compatible with Ribosome Display Systems

New plasmid vectors (pWRIL-1 and pWRIL-2) were designed to combine optimal functional features for phage display with compatible restriction sites that facilitate the "batch" transfer of selected protein-encoding sequences into compatible vectors designed for ribosomal protein display (e.g., pWRIL-3 and pWRIL-4, as described in Examples 2).

The new phage display vectors, pWRIL-1 and pWRIL-2, SEQ ID NO. 1 and 2, respectively, are designed to contain dual Sfi I restriction sites for cloning sequences encoding the polypeptide to be displayed or expressed. The two Sfi I restriction sites were designed to be non-compatible with each other during ligation reactions and were incorporated in functional regions of the expression cassette.

pWRIL-1 contains a restricted Lac promoter/operator system with upstream laI repressor sequence. pWRIL-2 differs from pWRIL-1 in the promoter region. pWRIL-2 further contains a strong tHP terminator inserted between the lacI gene and the Lac promoter/operator region, resulting in a very tightly regulated promoter/operator system. Additionally, a low efficiency ribosome-binding sequence is used in pWRIL-2 to further decrease g3-fusion protein production before induction. The different design of the promoter region for pWRIL-1 and pWRIL-2 is important. For example, pWRIL-2 will be particularly useful for the display of proteins that are toxic to E. coli because of its highly restricted promoter system, while pWRIL-1 is a more effective expression vector. Additionally, both pWRIL-1 and pWRIL-2 contain an Omp A leader peptide which drives the secretion of expressed protein into the periplasm.

A large (1.2 kb) "stuffer" sequence occupies the space between the two Sfi 1 restriction sites in both pWRIL-1 and pWRIL-2. This stuffer sequence includes a chloramphenicol resistance gene, which allows double antibiotic selection of bacteria after transformation with plasmid not yet containing a cloned sequence encoding a displayed protein. The stuffer sequence is also used for practical benefit, making double-cut plasmid easily distinguishable from single-cut plasmid during agarose gel purifications. In some embodiments, the stuffer sequence between the two non-compatible restriction sites comprises a nucleotide sequence that codes for an antibiotic resistance gene under a separate promoter than that which drives expression of a coding sequence of an antigen binding polypeptide of interest.

A hexa-histidine "tag" is designed to be contiguous to the C-terminal end of the cloned polypeptide, facilitating both affinity purification and detection of expressed proteins. A C-Myc epitope peptide tag is designed to be contiguous to the C-terminal end of the cloned protein after the polyhistidine tag, facilitating sensitive detection of expressed proteins.

A short amino acid sequence containing a trypsin cleavage site is inserted between the hexa-histidine and C-Myc tags. The trypsin cleavage site allows enzymatic elution of phage after selection, which is beneficial because the elution will not be affected by the affinity or stability of protein interactions.

Both pWRIL-1 and pWRIL-2 contain a truncated g3 sequence "stump" that encodes a C-terminal portion of the M13 bacteriophage coat protein 3 including g3 amino acids 250-406 (SEQ ID NO. 51). This g3 sequence "stump" is shorter than the more commonly used amino acids 198-406 construct. The shorter sequence removes a potentially unstable GS-rich linker region and the unpaired cysteine residue C201 that may cause aberrant Cys-Cys linkage during expression.

An "amber" DNA codon (nucleotide sequence TAG) is inserted between the C-Myc tag and the g3 stump. This codon is generally read as a stop codon by E. coli, but in male mutant "suppressor" strains (e.g., the supE or supF genotypes), this codon is frequently read as an amino acid, leading to read-through and expression of a protein-tag-g3 stump fusion-product, thereby allowing display of the fusion product on phage. Suppression of the amber codon is only partially effective, which is advantageous in phage display because it minimizes production of the g3 product, which is often toxic in E. coli. In "non-suppressor" strains, the stop codon is fully functional, resulting in free, tagged, proteins without fusion to the g3 stump.

Both pWRIL-1 and pWRIL-2 contain an F1 origin, the M13 bacteriophage origin of replication, which leads to packaging of the plasmid into phage particles, creating the critical phenotype to genotype linkage required for phage-display.

The vectors also contain an ampicillin resistance gene for antibiotic selection of E. coli transformed with the plasmid and a pUC origin or replication for propagation of the plasmid in E. coli.

The pWRIL-1 and pWRIL-2 vector systems are designed to facilitate the cloning of protein libraries or single clones using a single restriction enzyme such as SfiI and to allow efficient display of proteins on the surface of bacteriophage M13 and efficient expression of selected protein-encoding sequences from the same vector used for selection.

Moreover, pWRIL-1 and pWRIL-2 vector systems allow rapid reformatting into compatible vectors without altering gene sequence. In particular, the pWRIL-1/2 cloning regions have been designed to allow rapid and transfer of encoding sequences to and from ribosome display vectors of the present invention, such as, pWRIL-3 and pWRIL-4 (see Example 2). This is important for the analysis of ribosome display products as the vectors for ribosomal display are typically not compatible with bacterial expression of protein for further analysis.

Example 2

Design of Ribosome Display Vectors Compatible with Phage Display Systems

Two vectors pWRIL-3 and pWRIL-4 are designed to be compatible with phage display vectors, thereby facilitating transfer "en masse" between phage display and ribosome display systems.

As discussed above, an important feature of ribosome display vectors is the absence of a stop codon in the protein encoding sequence which causes ribosomes to stall whilst synthesizing the folded protein, thus forming a stable linkage between the ribosome, mRNA and encoded protein. Both pWRIL-3 and pWRIL-4 lacks a stop codon in-frame of the displayed polypeptide.

pWRIL-3 and pWRIL-4 contain restriction sites that are compatible with the phage display vectors of the present invention, for example, pWRIL-1 and pWRIL-2 (see Example 1). Specifically, both pWRIL-3 and pWRIL-4 contain two non-compatible SfiI sites that are present in phage display vectors such as pWRIL-1 and pWRIL-2. This feature allows libraries of antibodies and other proteins to be transferred "en masse" between phage display and ribosome display systems.

In addition, both pWRIL-3 and pWRIL-4 contain a 69 amino acid spacer polypeptide sequence (i.e., residues 249-318 of gene III) that separates displayed polypeptide from ribosome facilitating the correct folding of the polypeptide.

pWRIL-3 contains 5' and 3' stem loop structures to protect synthesized mRNA, a T7 promoter and ribosome binding site for in vitro transcription and translation in prokaryotic (Eschericia coli) lysates. Therefore, pWRIL-3 is most suitable for prokaryotic display. pWRIL-4 contains a 3' stem loop structure to protect synthesized mRNA and a T7 promoter and translational enhancer of *X. leavis* β globin gene for in vitro transcription and translation in Eukaryotic (Rabbit Reticulocyte) Lysates. Therefore, pWRIL-4 is most suitable for eukaryotic display.

Example 3

Reformatting and Mutagenesis of Parental Humanized XT-M4 as an ScFv Antibody

An anti-RAGE antibody, XT-M4, has previously been described in U.S. Patent Publication No. 200710286858A1, including chimeric and humanized version. A particular scFv humanized variant of XT-M4 (i.e., $V_H$ 2.0, $V_L$ 2.11) was also described in U.S. 2007/0286858A1 Reformatting and Mutagenesis of Parental Humanized XT-M4 as an ScFv Antibody Prior to mutagenesis and testing for improved potency the parental antibody XT-M4 was reformatted as an scFv in both the $V_L$-$V_H$ format and the $V_H$-$V_L$ format, incorporating a flexible linker sequence [DGGGSGGGGSGGGGSS; SEQ ID NO:16]. Both formats were functional, but the $V_L$-$V_H$ format was chosen for optimization. Restriction sites were also incorporated at either end of XT-M4 scFv to facilitate convenient reformatting to scFv-Fc fusion proteins utilizing general recombinant DNA techniques well known to those skilled in the art. Assembled scFv antibody fragments were synthesized from overlapping oligonucleotides, digested with Sfi1 restriction enzyme and cloned into the phage display vector pWRIL-1.

Parental antibody in the scFv format was mutagenized and screened for improved potency. Mutagenesis was performed using standard techniques, including oligonucelotide site-specific and error-prone PCR mutagenesis. Libraries of mutant clones were selected for increased antigen binding utilizing either Phage Display or Ribosome Display technology. A Ribosome Display library of variants was created by error prone PCR. This allowed the introduction of diversity over the whole length of the molecule and allowed the isolation of potentially beneficial mutations in CDRs other than VH-CDR3, framework residues and vernier regions. This approach is analogous to the natural process of somatic hypermutation. An added feature of this approach is the potential mapping of the functional antibody paratope, the definition of mutational 'Hotspots' and potential isolation of mutations that enhance VH/VL domain interactions. Due to the huge molecular diversity that can be generated by error prone PCR, this approach was only used in conjunction with ribosome display.

The XT-M4-error prone PCR product was cloned into the ribosome display vector, pWRIL-3 and had an estimated size of $5 \times 10^{12}$. Two phage display libraries were constructed targeting diversity into either the VH-CDR3 loop or the VL-CDR3 loop. The VH-CDR3 was aggressively mutated using total randomization using sequential NNS mutagenic codons spanning the length of the VH-CDR3 in blocks of two stretches of 6 codons overlapping by two codons to cover the VH-CDR3 of length 10 codons. The VL-CDR3 was subjected to a lower mutational load and a codon based strategy was taken. This approach aimed to mimic the natural amino acid diversity at each position within this loop using collated sequence alignment of natural V genes in the public database. The $V_H$-CDR3 randomized library had a size of $1.2 \times 10^9$ and the $V_L$-CDR3 based library was $5 \times 10^8$. The frequency and distribution of mutations in both CDR3 libraries (determined by sequencing), was consistent with the theoretical diversity introduced by the oligonucleotide design.

Example 4

Selection of scFv clones with improved affinity for human and mouse RAGE

Figure 6:
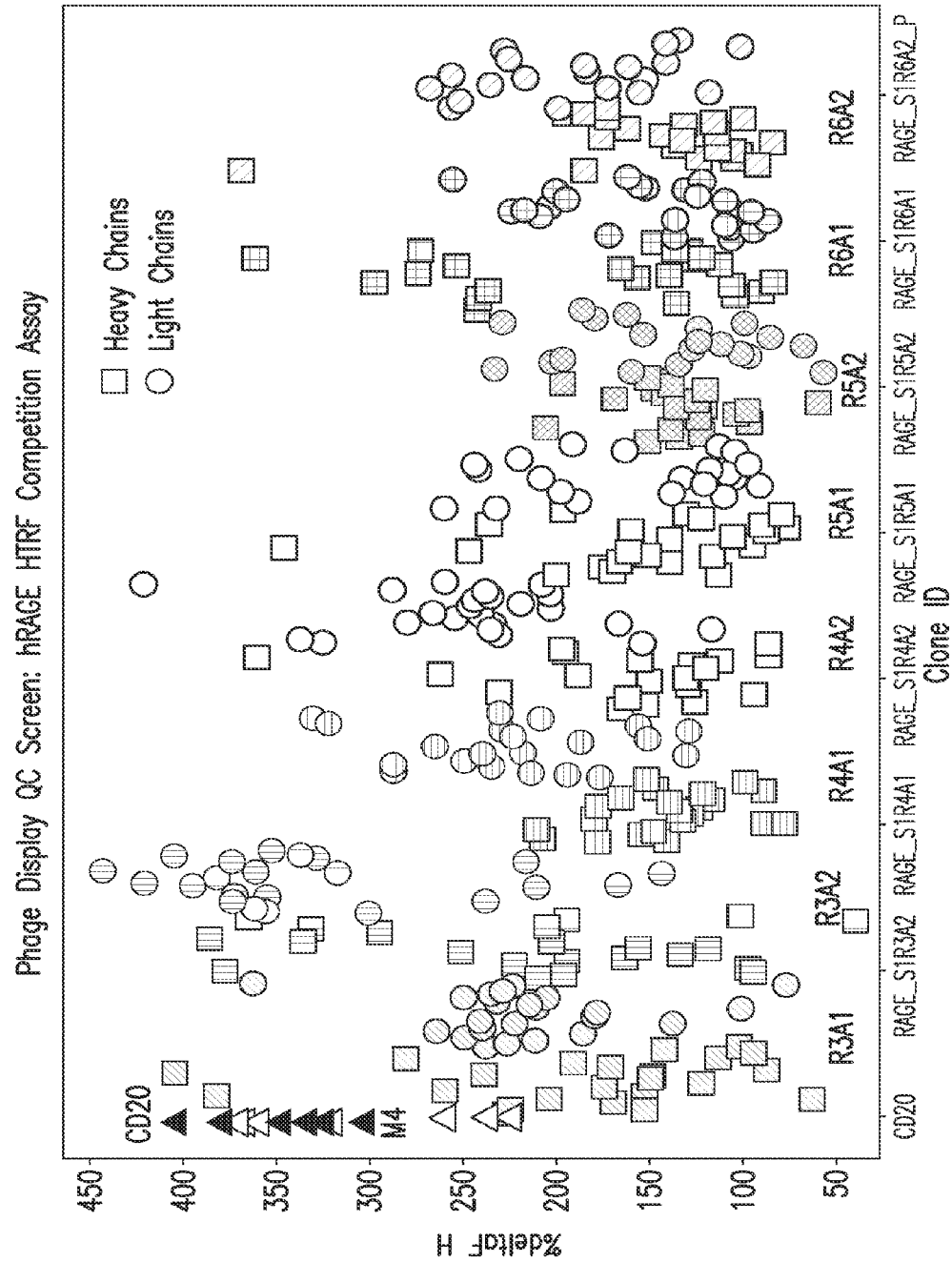
FIG. 6 represents results of initial screening for increased RAGE binding of scFV ribosome display clones.

Increases in binding to RAGE antigen were detected with the aid of a competition assay using parental XT-M4 antibody. Both phage display and ribosome display libraries were selected for affinity improved variants by incubating with biotin labeled hRAGE-Fc, recovering binding clones using streptavidin magnetic beads and washing away non binding variants. Sequential rounds of selection were carried on decreasing antigen concentrations to drive the preferential recovery of higher affinity variants. Clones recovered after selection were subsequently screening for improved binding to hRAGE-Fc using HTRF. This is an assay that measures the decrease in fluorescence upon binding of parental europium cryptate-labeled XT-M4 to RAGE in the presence of competing test scFv antibodies. In these assays, periplasmic preparations of scFv were prepared from bacterial cultures and added in increasing concentrations to a combination of parental antibody and antigen. The ability of the scFV to compete with parental XT-M4 antibody to bind to Biotin-labeled RAGE-Fc was determined. In the presence of avidin-XL665 complex labeled XT-M4 bound to biotinylated RAGE-FC was detected by Fluorescence. Increasing amounts of scFv that competed with the XT-M4 for binding to biotinylated-RAGE-Fc was detected as a decrease in fluorescence. A sequential process of screening was used to focus in on a smaller number of clones with the greatest competition in HTRF assay High-throughput HTRF analysis of individual rounds of selections on human RAGE for Phage Display clones is shown in FIG. 6. Empty triangles represent parental XT-M4 scFv. Filled triangles represent negative control anti CD20 scFv. Circles represent clones derived from the VL-CDR3 library and squares represent clones derived from the VH-CDR3 libraries. All analyses were carried out as single point assays using unpurified periplasmic preparations of scFv proteins. Clones towards the top of the figure are negative non binding clones and as selections proceed from left to right the number of non binding clones decreases.

Figure 7:
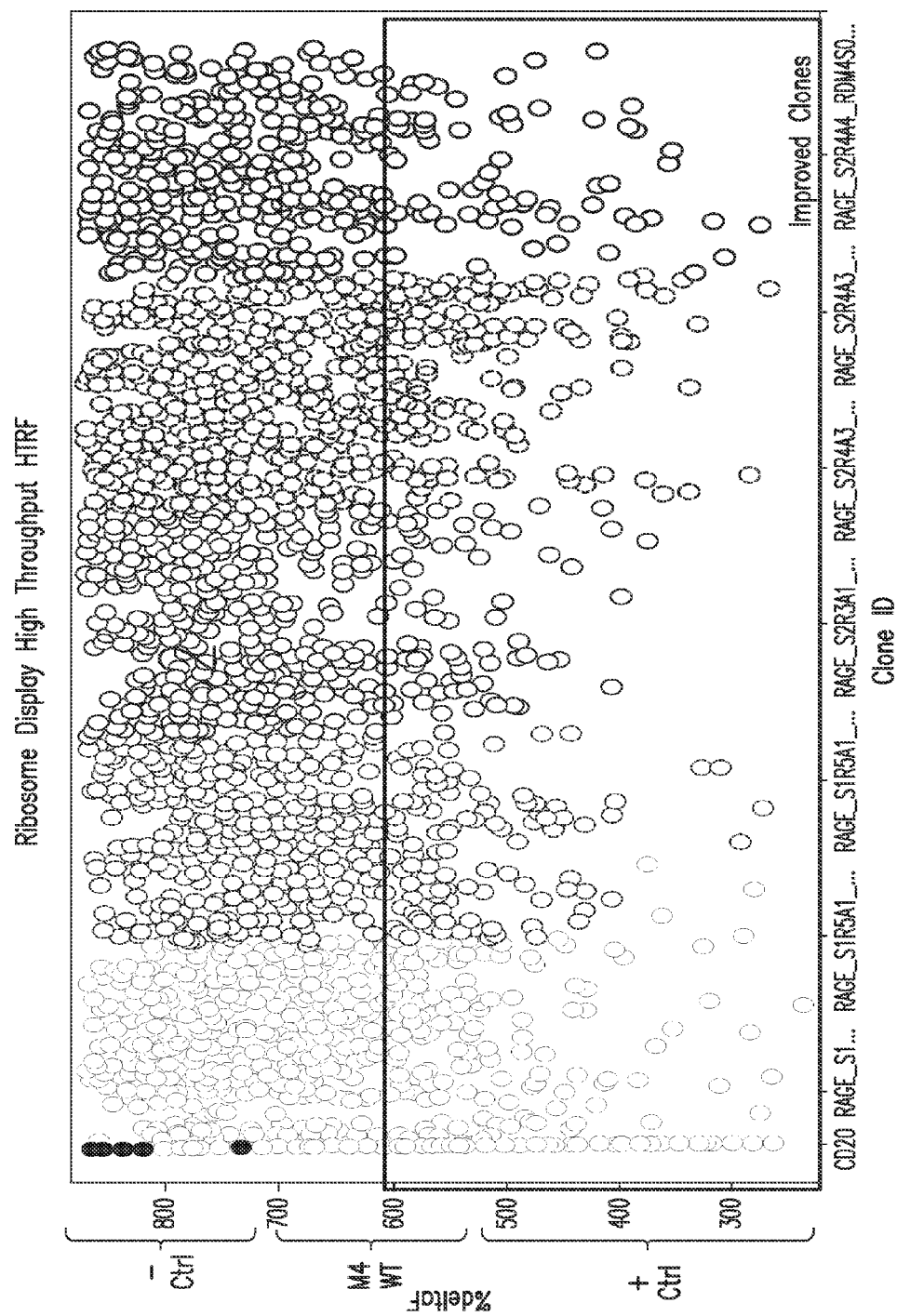
FIG. 7 represents results of initial screening for increased RAGE binding of scFv phage display clones.

High-throughput HTRF analysis of individual rounds of selections on human RAGE are shown for ribosomal display clones in FIG. 7. Range of negative control (CD20 ScFv, parental wild-type (XTM4 scFv) and positive control (H8 ScFv) are indicated on the y axis which measures the change in fluorescence in competition HTRF. The clones with improved binding are boxed.

An increase in the number of highly competing clones retrieved was observed after each round of selection, when compared to parental XT-M4 scFv.

Selected $V_L$-CDR3 variants were found to be less potent than the $V_H$-CDR3 variants, suggesting a greater importance of the $V_H$-CDR3 in determining antigen binding. It was also observed that the GGDI motif at the 5' end of the $V_H$-CDR3 sequence was not tolerant of mutation (an observation further confirmed using ribosome display strategy). A particular mutation in the heavy chain CDR3, F106L, was identified in the $V_H$-CDR3 that was present in the vast majority of selected variants. F106I was also observed in several clones, but this mutation was not associated with the same affinity gains observed for F106L. Sequence analysis of improved variants showed that there were several distinct families of clones.

A large family of closely related improved clones was found to have a "charge-hydrophobe-small" motif in the center of the loop (positions 103,104,105), predominantly comprised of K/R-V-G/S sequences. A second family of improved clones had a different motif at positions 103-105; comprised of 'hydrophobe-charge-small' (L/V-D-S/G), or 'hydrophobe-hydrophobe-small' (L-V-G/S) sequences. In almost all clones sequenced there was a preference for a small amino acid (S, G, occasionally M) at position 105. This represents maintenance of the wild-type amino acid chemistry at this position. The T103K/R/L and T104V/D mutations represent significant changes in chemistry at these positions. The vast majority of improved clones exhibited a preference for a charged residue (D, R, H) to the c-terminal side of F106L (position 107), with the natural amino acid at this position (D) being predominantly preferred. However, the highest overall affinity clone identified (clone 3G5) carries a proline in this position. The last position in the CDR3 (Y108) was generally variable amongst the total population, but was mostly maintained as one of the large aromatic residues most often found at this position in natural antibodies (Y, F). Gains in affinity were somewhat less successful in the VL than the VH. Tables 3 and 4 below represent Phage Display (Table 3) and Ribosome Display (Table 4) clones that were selected for increased affinity for RAGE binding. Clones highlighted with an "*" in Table 3 and all clones except S2R4A4_6G2 in Table 4 were reformatted as scFv-Fc fusions.

TABLE 3

IC50 VALUES FOR PHAGE DISPLAY CLONES.
"X" REPRESENTS ANY AMINO ACID

| Clone ID | LCDR3 | HCDR3 | IC$_{50}$ (nM) |
| --- | --- | --- | --- |
| M4WT | LEFDEHPLT (SEQ ID NO. 17) | GGDITTGFD (SEQ ID NO. 32) | 33.2 |
| 3A10 | LEFSLSRS (SEQ ID NO. 18) | | Nd |
| 3B7 | LQFDSHPLT (SEQ ID NO. 19) | | 7.35 |
| 3B9 | LQFDNHPLT (SEQ ID NO. 20) | | 10.59 |
| 3C7 | LQYDAHPXT (SEQ ID NO. 21) | | 9.23 |
| 3E8 | LQFDVHPLT (SEQ ID NO. 22) | | 7.21 |
| 3G8 | LQYDAHPLT (SEQ ID NO. 23) | | 8.08 |
| 6A8 | XXFXXHPLT (SEQ ID NO. 24) | | 3.14 |
| 6A10 | LQFDAHPLT (SEQ ID NO. 25) | | 6.94 |
| 6A11 | LQFDSHPLT (SEQ ID NO. 26) | | 32.75 |
| 6A12 | LQYDAHPLT (SEQ ID NO. 27) | | 8.27 |
| 6B8 | XXFDXHPLT (SEQ ID NO. 28) | | 3.34 |
| 6C1 | LELDEHPLT (SEQ ID NO. 29) | | 4.44 |
| 6C10 | LQFDEHPLT (SEQ ID NO. 30) | | 7.38 |
| 6C11 | LQYDAHPLT (SEQ ID NO. 31) | | 9.03 |
| 3A6* | | GGDILVSLDV (SEQ ID NO. 33) | 0.47 |
| 3B2* | | GGDILVGLDY (SEQ ID NO. 34) | 0.91 |
| 3B4* | | GGDIREGLRY (SEQ ID NO. 35) | 1.30 |
| 3C6 | | GGDIVVGLDH (SEQ ID NO. 36) | 1.25 |
| 3D2* | | GGDIRVSLDH (SEQ ID NO. 37) | 1.27 |
| 3D5 | | GGDIKVGLDL (SEQ ID NO. 38) | 2.99 |
| 3D6 | | GGDIRVMLDL (SEQ ID NO. 39) | 2.92 |
| 3G3 | | GGDIKVSLDH (SEQ ID NO. 40) | 1.44 |
| 3G5* | | GGDILDSLPY (SEQ ID NO. 41) | 0.87 |
| 6B2* | | GGDIRVGLDV (SEQ ID NO. 42) | 1.77 |
| 6B6* | | GGDIIISLDW (SEQ ID NO. 43) | 0.64 |
| 6C1 | | GGDIKVGLDN (SEQ ID NO. 44) | 4.44 |

TABLE 3-continued

IC50 VALUES FOR PHAGE DISPLAY CLONES. "X" REPRESENTS ANY AMINO ACID

| Clone ID | LCDR3 | HCDR3 | IC$_{50}$ (nM) |
|---|---|---|---|
| 6C2* | | GGDIKVSLDR (SEQ ID NO. 45) | 0.73 |
| 6C3* | | GGDITLGLDV (SEQ ID NO. 46) | 1.52 |
| 6D5 | | DDDIKVSLDQ (SEQ ID NO. 47) | 1.45 |
| 6E3 | | GGDIRVSLDF (SEQ ID NO. 48) | 1.74 |
| 6E5 | | GGDIRVMLDV (SEQ ID NO. 49) | 2.25 |
| 6G4* | | GGDILDSLHF (SEQ ID NO. 50) | 2.03 |

TABLE 4

IC50 VALUES FOR RIBOSOME DISPLAY CLONES

| Clone | IC50 (nM) |
|---|---|
| XT-M4 | 33.0 |
| S2R4A4_6G2 | 1.3 |
| S2R4A3_10H6 | 0.3 |
| S2R3A1_8G9 | ~2.4 |
| S2R4A3_10D8 | 2.6 |
| S1R5A1_3B3 | 2.2 |
| S2R4A4_1G6 | 1.2 |
| S2R3A1_2E6 | 1.9 |
| S2R4A3_5A3 | ~3.0 |
| S1R5A1_10G10 | 16.3 |
| S2R3A1_5H3 | 8.2 |

Sequence analysis of 261 Ribosome Display clones from sequential rounds of selection with functional binding to coated hRAGE-Fc in ELISA showed a diverse spread of mutations in both the $V_H$ and $V_L$ domain distributed across both CDR's and the framework regions. Furthermore, residues were defined that do not tolerate mutations. Some evidence of dominant mutations that were carried through consecutive rounds of selection was also identified, indicating selective pressure for certain clones.

Example 5

Reformatting Of Scfv Clones To Scfv-Fc Fusion Proteins

Clones identified from phage display and ribosome display selections were chosen for scFv-Fc reformatting. In the case of the ribosome display clones in pWRIL-3 as described above, other secondary criteria were also considered in order to make the top 10 selection (i.e. clones had to have a mutation with an amino acid frequency of >4 in the population of 123 sequences, clones carrying frequently occurring mutations and clones considered to be carrying mutations potentially positioned at the $V_L/V_H$ interface). The initial design of the parental XT-M4 scFv construct incorporated BssHII and Bcl1 restriction sites at the 5' and 3' end of the scFv sequence in pWRIL-3 to facilitate direct reformatting into Fc fusions using the chosen acceptor vector.

The acceptor vector contained a wildtype (wt) IgG constant region (Fc), with a eukaryotic promoter and eukaryotic and bacterial origins of replication for transfer and expression in bacteria and eukaryotic organisms. It also contained a multiple cloning site for integration of one or more variable region binding domains and allows for expression of the variable region(s) as part of an FV-Fc fusion protein. Nucleic acids encoding selected scFv were cloned into pre-the pSMED vector operably linked and fused at the protein level with an Fc constant region. The recombinant plasmid contained an open reading frame comprising the scFv coding region amino to the Fc region containing protein coding sequences for the hinge region followed by the CH1 and CH2 regions of a human IgG.

The recombinant plasmid described above was transfected into COS cells and the scFv-Fc fusions constructs were expressed. Following expression in COS cells, the scFv utilizes the dual hinge regions to form a bivalent scFv-Fc fusion construct. The panel of selected clones derived by phage display (n=10) and ribosome display (n=10) were converted to Fc fusions as described above for the parent XT-M4 [Note: one of the ribosome display clones was lost due to the generation of a internal Bcl1 site by random mutagenesis].

These were expressed transiently in COS cells and purified by Protein A affinity chromatography, followed by buffer exchange into PBS. SDS-PAGE analysis of the purified proteins indicated that the level of purity was high and did not detect any obvious aggregation or degradation products. SEC (size exclusion chromatography) analysis of each of the clones was also carried out to detect formation of high molecular weight aggregates (HMW). Overall, the level of HMW formation was low for both phage display and ribosome display clones. The ribosome display clones discovered herein in particular have a very favorable SEC profile with low levels of aggregation. Without being bound by theory, low level aggregation may be due to the fact that these scFv molecules have been subjected to random error-prone PCR across the whole length of the sequence and in this sense have evolved as a single unit. Clones 10H6, 10D8 and 2E6 carried a mutation in the flexible linker to Asn residue which could also be correlated with improved biochemical characteristics. For SEC analysis of scFv-Fc fusion proteins. All samples were run at a concentration of 60 µg/ml in 50 mM sodium phosphate buffer, pH 7.5.

Figure 8A:
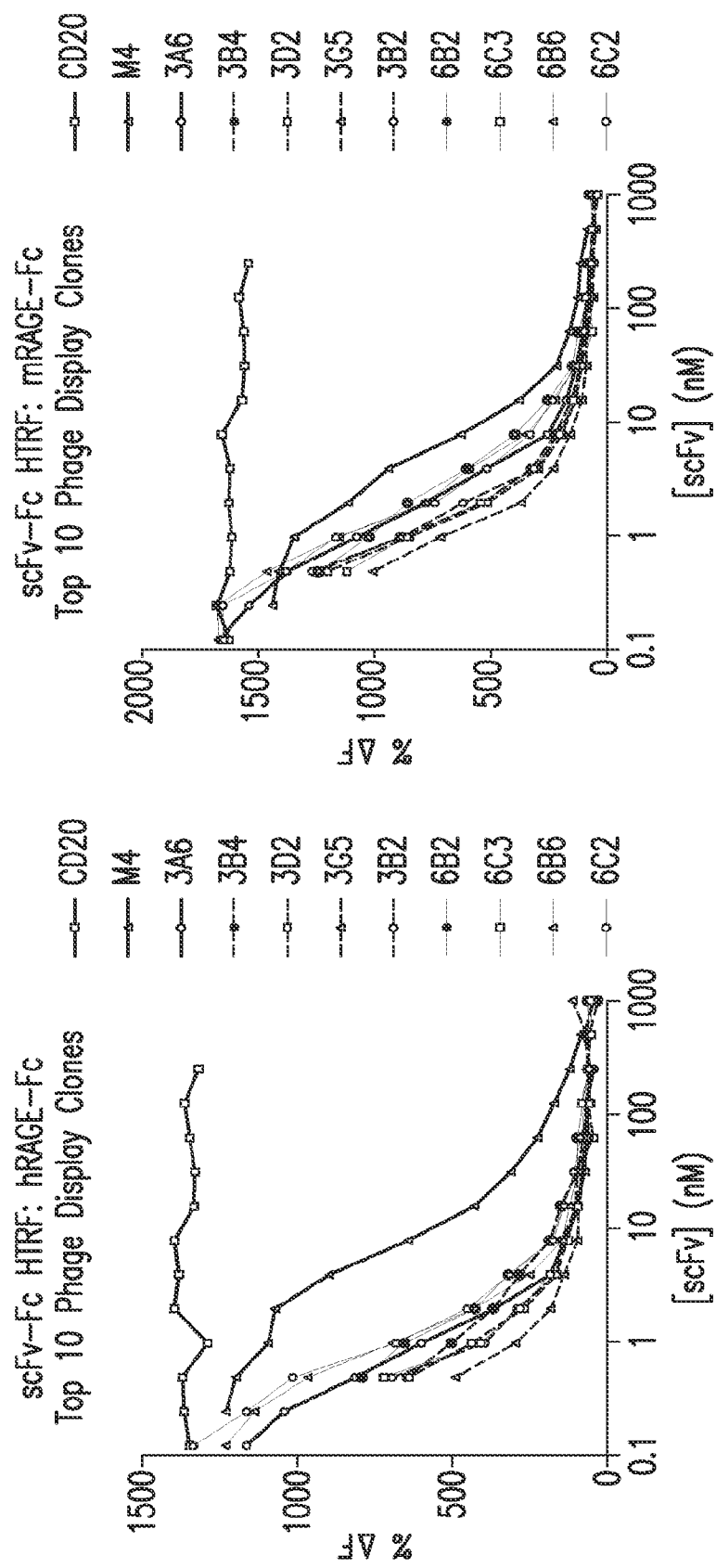
FIGS. 8A and 8B represent results of HTRF analysis of recombinant scFv-Fc fusions binding to murine and human RAGE.
Figure 8B:
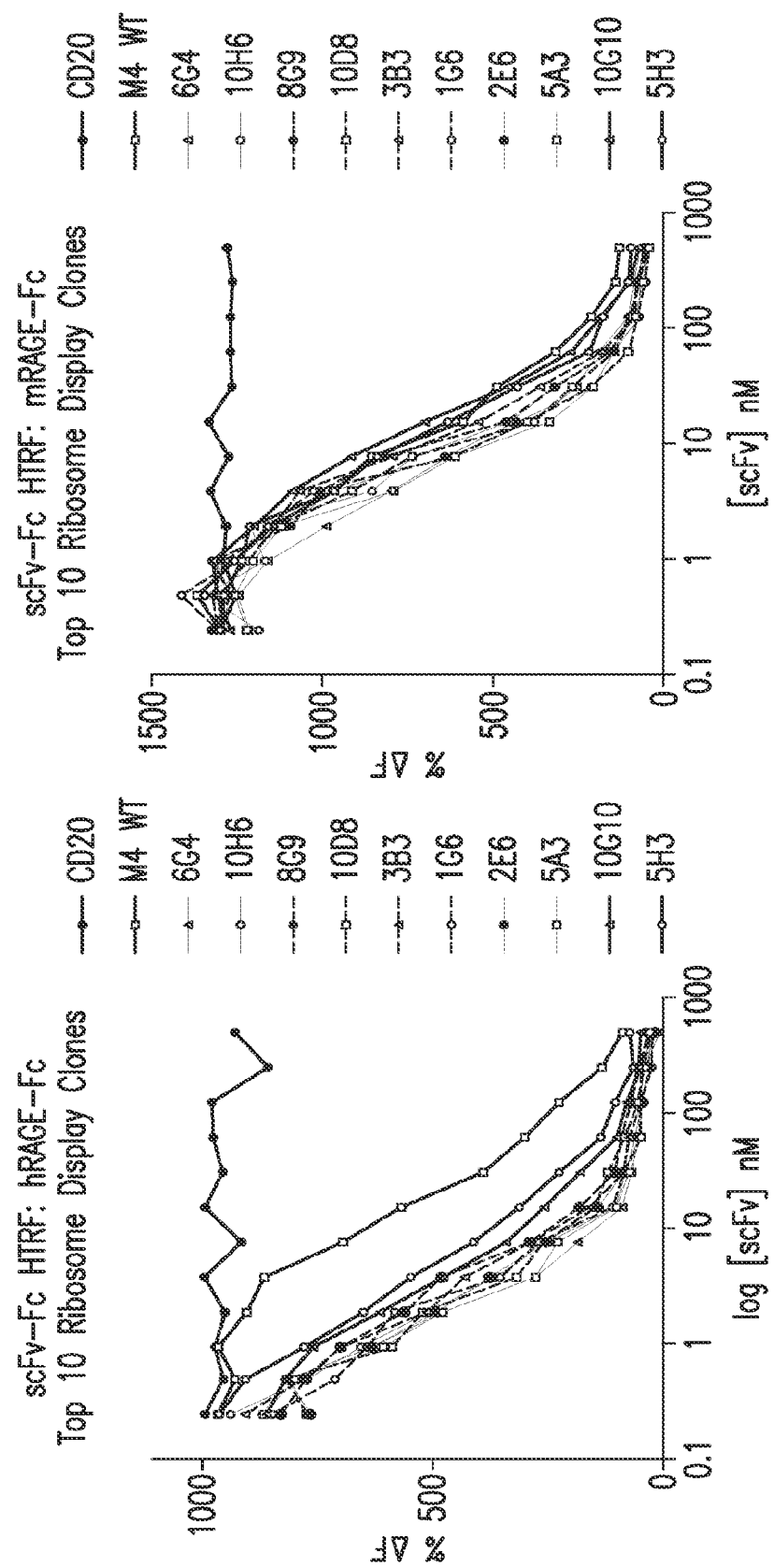
Figure 9:
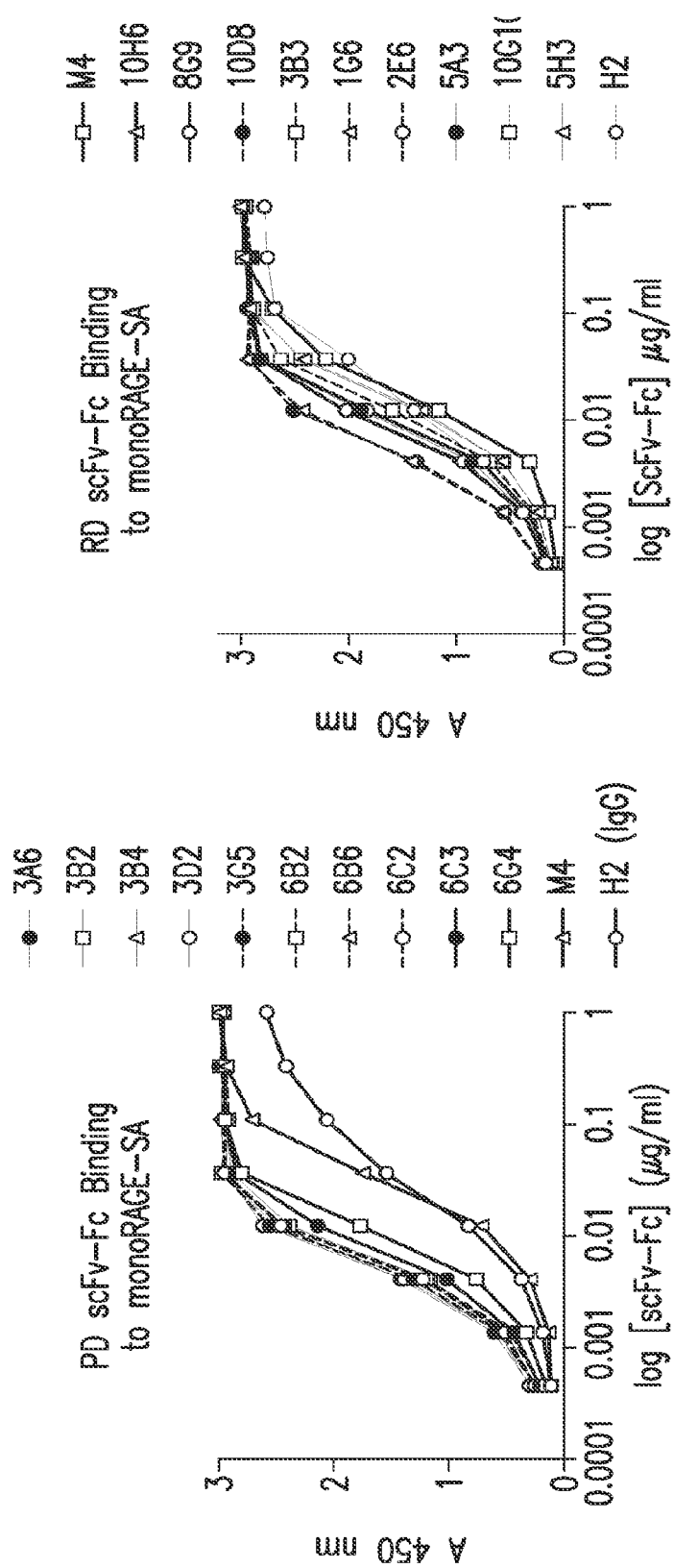
FIG. 9 represents results of HTRF analysis of recombinant scFv-Fc fusions binding to human soluble RAGE.

Purified scFv-Fc proteins were also subjected to HTRF titration as above and this confirmed affinity improvements in a bivalent format. In most cases further improvements were seen in going from scFv to a bivalent fusion. Both phage and ribosome display clones showing improved potency were reformatted to scFv-Fc fusions. The HTRF titration analysis was carried out for both human and murine RAGE as shown in FIGS. 8A and B and FIG. 9.

Example 6

Characterization Of Scfv-Fc Fusion Proteins

BIAcore analysis and kinetic constant calculation used RAGE-SA directly immobilized on a CM5 BIACORE surface with scFv-Fc proteins injected over the surface for 3 min with a dissociation period of 5 min. In summary, mutant clones were significantly improved with improvements in kd values ranging from 7 to 69 fold for the phage display clones and 4 to 67 fold for the ribosome display clones. T Example 7

Binding Of Scfv-Fc Proteins To Cho-Rage Cells

Binding of scFv-Fc proteins to CHO-RAGE cells was conducted to ensure that selected clones also exhibited improved binding to authentic cell surface expressed RAGE target. Improved EC50 values were observed of between 5-14 fold over parental XT-M4 scFv-Fc fusions. Stably transfected Chinese Hamster Ovary (CHO) cells were engineered to express murine and human RAGE full length proteins. The murine and human RAGE cDNAs were cloned into the mammalian expression vector pSMED, linearized and transfected into CHO cells using lipofectin methods (Kaufman, R. J., 1990, *Methods in Enzymology* 185:537-66;

Kaufman, R. J., 1990, *Methods in Enzymology* 185:487-511; Pittman, D. D. et al., 1993, *Methods in Enzymology* 222: 236). Cells were further selected in 20 nM methotrexate and cell extracts were harvested from individual clones and analyzed by SDS sodium dodecyl sulfate-polyacrylamide gel electrophoresis (SDS-PAGE) and Western blotting to confirm expression. These results are shown below in Table 11. Absorbance 450 nm values were corrected for the same clones binding to control CHO cells not expressing RAGE. EC50 values were calculated after curve fitting using Graph-Pad prism and are expressed in µg/ml. EC50 is the effective concentration that gives 50% of maximum value in ug/ml of scFv-Fc protein.

TABLE 5

| Clone ID Phage Display | EC50 | Clone ID Ribosome display | EC50 |
|---|---|---|---|
| H2 IgG | 0.068 | H2 IgG | 0.0897 |
| M4 IgG | 0.312 | M4 IgG | 0.266 |
| M4 scFv-Fc | 0.408 | M4 scFv-Fc | 0.388 |
| 3A6 | 0.0673 | 8G9 | 0.077 |
| 3B2 | 0.0335 | 10D8 | 0.092 |
| 3D2 | 0.1363 | 1G6 | 0.1875 |
| 3G5 | 0.0565 | 2E6 | 0.1134 |
| 6B2 | 0.0816 | 5A3 | 0.096 |
| 6C2 | 0.0285 | 10G10 | 0.1334 |
| 6C3 | 0.155 | IgG control | N/A |
| 6B6 | 0.0285 | 3B3 | 0.541 |
| 6G4 | 0.1721 | | |

What is claimed is:

1. A polynucleotide comprising the sequence of SEQ ID NO:1 (pWRIL-1 sequence).

2. The polynucleotide of claim 1 further comprising an insert.

3. The polynucleotide of claim 2, wherein the polynucleotide does not include a stuffer sequence.

4. The polynucleotide of claim 3, wherein the polynucleotide does not include the stuffer sequence from nucleotide 2865 to nucleotide 4001 of SEQ ID NO:1.

5. The polynucleotide of claim 4 further comprising an insert.

6. The polynucleotide of claim 5, wherein the insert is cloned in using a SfiI restriction enzyme.

7. A cell comprising the polynucleotide of claim 6.

8. The polynucleotide of claim 6, wherein the insert comprises a polynucleotide encoding an antigen binding polypeptide.

9. The polynucleotide of claim 8, wherein the antigen binding polypeptide is selected from the group consisting of a peptide, a chimeric antibody, a humanized antibody, a human antibody, a single chain antibody, a tetrameric antibody, a tetravalent antibody, a multispecific antibody, a domain-specific antibody, a domain-deleted antibody, a fusion protein, an ScFc fusion protein, an Fab fragment, an Fab' fragment, an F(ab')2 fragment, an Fv fragment, a single-chain Fv fragment (ScFv), an Fd fragment, a single domain antibody, a dAb fragment, a small modular immunopharmaceutical, a shark variable IgNAR domain, a CDR3 peptide, a constrained FR3-CDR3-FR4 peptide, a nanobody, a bivalent nanobody, a minibody, a full-length light antibody chain, a full-length heavy antibody chain, a variable light domain, and a variable heavy domain.

10. The polynucleotide of claim 9, wherein the antigen binding polypeptide is a single-chain Fv antibody.

* * * * *